(12) United States Patent
Gopal et al.

(10) Patent No.: US 8,434,489 B2
(45) Date of Patent: May 7, 2013

(54) CONTRACEPTIVE DEVICES AND METHODS

(75) Inventors: Vidya Gopal, Fremont, CA (US); Christopher Stout, San Bruno, CA (US); Betsy Swann, Grass Valley, CA (US)

(73) Assignee: Conceptus, Inc., Mountain View, CA (US)

( * ) Notice: Subject to any disclaimer, the term of this patent is extended or adjusted under 35 U.S.C. 154(b) by 349 days.

(21) Appl. No.: 12/605,304

(22) Filed: Oct. 23, 2009

(65) Prior Publication Data

US 2011/0094519 A1    Apr. 28, 2011

(51) Int. Cl.
*A61F 6/06* (2006.01)
*A61M 29/00* (2006.01)

(52) U.S. Cl.
USPC ............................ 128/831; 128/830; 606/200

(58) Field of Classification Search .......... 128/830–841; 604/28, 53, 32, 36, 108, 158, 213; 606/28, 606/53, 200, 192, 193, 197, 198; 424/422, 424/426, 430, 423, 424; 623/1.11, 1.12, 623/23.7
See application file for complete search history.

(56) References Cited

U.S. PATENT DOCUMENTS

| | | |
|---|---|---|
| 3,640,741 A | 2/1972 | Etes |
| 3,865,108 A | 2/1975 | Hartop |
| 3,991,766 A | 11/1976 | Schmitt et al. |
| 3,992,562 A | 11/1976 | Denzinger et al. |
| 4,002,173 A | 1/1977 | Manning et al. |
| 4,014,335 A | 3/1977 | Arnold |
| 4,207,893 A | 6/1980 | Michaels |
| 4,509,504 A | 4/1985 | Brundin |
| 5,171,148 A | 12/1992 | Wasserman et al. |
| 5,198,220 A | 3/1993 | Damani |
| 5,258,042 A | 11/1993 | Mehta |
| 5,350,397 A | 9/1994 | Palermo et al. |
| 5,382,259 A | 1/1995 | Phelps et al. |
| 5,410,016 A | 4/1995 | Hubbell et al. |
| 5,469,867 A | 11/1995 | Schmitt |
| 5,658,327 A * | 8/1997 | Altman et al. ............ 607/127 |
| 5,695,480 A | 12/1997 | Evans et al. |
| 5,826,584 A | 10/1998 | Schmitt |
| 6,015,424 A | 1/2000 | Rosenbluth et al. |

(Continued)

FOREIGN PATENT DOCUMENTS

| | | |
|---|---|---|
| WO | WO 99/15116 | 4/1999 |
| WO | WO 00/14139 | 3/2000 |
| WO | WO 2006/102329 A1 | 9/2006 |

OTHER PUBLICATIONS

Bhatia, et al., J. Biomater. Sci., Polym. Ed., 6(5):435 1994.

(Continued)

*Primary Examiner* — Patricia Bianco
*Assistant Examiner* — Ophelia A Hawthorne
(74) *Attorney, Agent, or Firm* — Blakely, Sokoloff, Taylor & Zafman LLP

(57) ABSTRACT

Contraceptive devices that provide substantially immediate and permanent sterilization are described herein. Systems and methods for transcervically delivering the contraceptive devices are also described herein. The contraceptive device may include an expandable implant. The implant includes hydrogel to provide substantially immediate sterilization, and tissue in-growth fibers to provide permanent sterilization. As an alternative or in combination to hydrogel, the implant may include copper or cupric ions to provide substantially immediate sterilization. The implant may also include hydrogel to improve trackability of the implant through an ovarian pathway.

49 Claims, 19 Drawing Sheets

U.S. PATENT DOCUMENTS

| | | | |
|---|---|---|---|
| 6,096,052 | A | 8/2000 | Callister et al. |
| 6,238,403 | B1 | 5/2001 | Greene, Jr. et al. |
| 6,299,619 | B1 | 10/2001 | Greene, Jr. et al. |
| 6,379,373 | B1 | 4/2002 | Sawhney |
| 6,526,979 | B1 * | 3/2003 | Nikolchev et al. ............ 128/830 |
| 6,605,294 | B2 | 8/2003 | Sawhney |
| 6,634,361 | B1 | 10/2003 | Nikolchev et al. |
| 6,705,323 | B1 | 3/2004 | Nikolchev et al. |
| 6,709,667 | B1 | 3/2004 | Lowe et al. |
| 6,723,108 | B1 | 4/2004 | Jones et al. |
| 6,763,833 | B1 | 7/2004 | Khera et al. |
| 7,025,990 | B2 | 4/2006 | Sawhney |
| 7,237,552 | B2 * | 7/2007 | Khera et al. ................. 128/830 |
| 2001/0046518 | A1 | 11/2001 | Sawhney |
| 2002/0013589 | A1 | 1/2002 | Callister et al. |
| 2002/0029051 | A1 | 3/2002 | Callister et al. |
| 2002/0120276 | A1 | 8/2002 | Greene, Jr. et al. |
| 2002/0177855 | A1 | 11/2002 | Greene, Jr. et al. |
| 2004/0009205 | A1 | 1/2004 | Sawhney |
| 2004/0059370 | A1 | 3/2004 | Greene, Jr. et al. |
| 2004/0098028 | A1 | 5/2004 | Martinez |
| 2004/0158282 | A1 | 8/2004 | Jones et al. |
| 2005/0061329 | A1 | 3/2005 | Tran et al. |
| 2005/0113859 | A1 * | 5/2005 | Elliott et al. ................. 606/197 |
| 2005/0171572 | A1 | 8/2005 | Martinez |
| 2005/0187561 | A1 | 8/2005 | Lee-Sepsick et al. |
| 2005/0192616 | A1 | 9/2005 | Callister et al. |
| 2005/0255091 | A1 | 11/2005 | Loomis |
| 2005/0274384 | A1 | 12/2005 | Tran et al. |
| 2006/0034930 | A1 | 2/2006 | Khosravi et al. |
| 2006/0052822 | A1 | 3/2006 | Mirizzi et al. |
| 2006/0052823 | A1 | 3/2006 | Mirizzi et al. |
| 2006/0058834 | A1 | 3/2006 | Do et al. |
| 2006/0148897 | A1 | 7/2006 | Vernon et al. |
| 2006/0149299 | A1 | 7/2006 | Greene, Jr. et al. |
| 2006/0193899 | A1 | 8/2006 | Sawhney |
| 2006/0293560 | A1 | 12/2006 | Nguyen et al. |
| 2007/0056591 | A1 * | 3/2007 | McSwain ...................... 128/831 |
| 2007/0227544 | A1 | 10/2007 | Swann et al. |
| 2008/0017201 | A1 | 1/2008 | Sawhney |
| 2009/0056722 | A1 | 3/2009 | Swann |
| 2009/0123519 | A1 | 5/2009 | Rolfes et al. |
| 2009/0232869 | A1 | 9/2009 | Greene, Jr. et al. |
| 2009/0266366 | A1 | 10/2009 | Swann et al. |
| 2010/0119451 | A1 | 5/2010 | Sawhney |
| 2011/0245863 | A1 * | 10/2011 | Martinez ...................... 606/200 |

OTHER PUBLICATIONS

Jarrett, et al., "Bioabsorbable Hydrogel Tissue Barrier: In Situ Gelation Kinetics,"Trans. Soc. Biomater., vol. XVIII, 182, 1995.

Park, "Enzyme-digestible swelling hydrogels as platforms for long-term oral delivery: synthesis and characterization" Biomaterials, 9:435-441, 1998.

Park, et al., "Biodegradable Hydrogels for Drug Delivery" Technomic Pub. Co., Lancaster, PA, 1993.

Sawhney, et al., "Bioerodible Hydrogels Based on Photopolymerized Poly(ethyleneglycol)-co-poly(.alpha.-hydroxy acid) Diacrylate Macromers" Macromolecules, 26:581-587 (1993).

Shalaby, "Encyclopedia of Pharmaceutical Technology" Boylan & Swarbrick, Eds., 1988, vol. 1, p. 465, Dekker, N.Y.

"Aquadapt Medical Hydrogels" prior to Oct. 23, 2009, Hydromer Inc.

"Loctite® 4541™ Technical Data Sheet" Dec. 2008, Henkel Corporation.

PCT International Search Report and Written Opinion for International Application No. PCT/US2010/049188, mailed Dec. 7, 2010, 16 pages.

Zollikofer, et al., "A Combination of Stainless Steel Coil and Compressed Ivalon: A New Technique for Embolization of Large Arteries and Arteriovenous Fistulas" Radiology, Jan. 1981, vol. 138, pp. 229-231.

PCT International Preliminary Report on Patentability for International Application No. PCT/US2010/049188, mailed May 3, 2012 (11 pages).

* cited by examiner

CONTRACEPTIVE DEVICES AND METHODS

FIELD

The present invention relates to the field of contraceptive devices and, in particular, to contraceptive devices including hydrogel.

BACKGROUND

Female contraception and/or sterilization may be affected by transcervically introducing an object (e.g. a coil) into a fallopian tube to inhibit conception. Devices, systems and methods for such a contraceptive approach have been described in various patents and patent applications assigned to the present assignee. For example, PCT Patent Application No. 99/15116, U.S. Pat. No. 6,526,979 and U.S. Pat. No. 6,634,361, which are hereby incorporated herein in their entirety, describe devices that are transcervically inserted into an ostium of a fallopian tube and mechanically anchored within the fallopian tube. The devices described in these patents and patent application may promote a tissue in-growth around and within the inserted device, which may be referred to as an implant or an insert. One example of such devices is the device known as "Ensure" from Conceptus, Inc. of Mountain View, Calif. This tissue in-growth tends to provide long-term contraception and/or permanent sterilization without the need for surgical procedures.

The tissue in-growth, however, is not immediate. Typically, physicians suggest patients wait about three months after insertion of the device for the long-term contraception and/or permanent sterilization based on tissue ingrowth to be effective. Patients often desire even more immediate results for permanent contraception and/or permanent sterilization.

SUMMARY OF THE DESCRIPTION

Various different embodiments are disclosed below and the following summary provides a brief description of only some of these embodiments.

In one embodiment, the present invention relates to a contraceptive device including an expandable implant having a proximal end and a distal end, wherein a portion of the expandable implant comprises hydrogel and tissue in-growth promoting fibers on the surface of and/or within the expandable implant. The hydrogel, after it expands within a fallopian tube, can create an impermeable barrier of the fallopian tube and hence effectively provide nearly immediate contraceptive effect by functionally blocking the fallopian tube into which it is implanted.

In another embodiment, the present invention relates to a contraceptive device including an inner coil; an expandable outer coil; a flexible tip; a distal solder joint connecting the outer coil, inner coil and flexible tip; a detachable release joint near a proximal portion of the contraceptive device; tissue in-growth promoting fibers between the inner coil and the expandable outer coil; and wherein one or more of the flexible tip, distal solder joint or detachable release joint comprises hydrogel.

In yet another embodiment, the present invention relates to a system for delivering an implant to an ovarian pathway of a female body including a delivery catheter having a distal end and a proximal end, the distal end of the catheter comprising a hydrophobic material; and an expandable implant releasably coupled with the catheter, the expandable implant including hydrogel and tissue ingrowth promoting fibers.

In a further embodiment, the present invention relates to a method including delivering a catheter having an expandable implant releasably coupled with the catheter, the expandable implant including hydrogel and tissue ingrowth fibers, to an ovarian pathway; and expanding the expandable implant in the fallopian tube.

In a further embodiment, a contraceptive device includes an expandable implant having fibers adapted to cause tissue ingrowth into the expandable implant and also having a hydrogel coupled to the expandable implant; the expandable implant and the hydrogel are surrounded by a delivery sheath which covers the hydrogel during delivery of the device so that the hydrogel does not become exposed to tissue fluids during delivery until the delivery sheath is retracted or otherwise removed.

In yet another embodiment, a contraceptive device includes an expandable implant having fibers adapted to cause tissue ingrowth into the expandable implant and a hydrogel is also coupled to the expandable implant, and the hydrogel is encapsulated within a coating (e.g. a hydrophobic coating) which rapidly degrades or dissolves in a physiological environment; such an embodiment can use a delivery system which does not include a sheath if the expandable implant can be delivered in a restrained (non-expanded) state without a sheath.

Various other devices and methods for using devices, including kits for use in treating patients, are also described below. Other features of the present invention will be apparent from the accompanying drawings and from the detailed description that follows.

BRIEF DESCRIPTION OF THE DRAWINGS

The invention is described by way of example with reference to the accompanying drawings, wherein.

DETAILED DESCRIPTION

Figure 1:
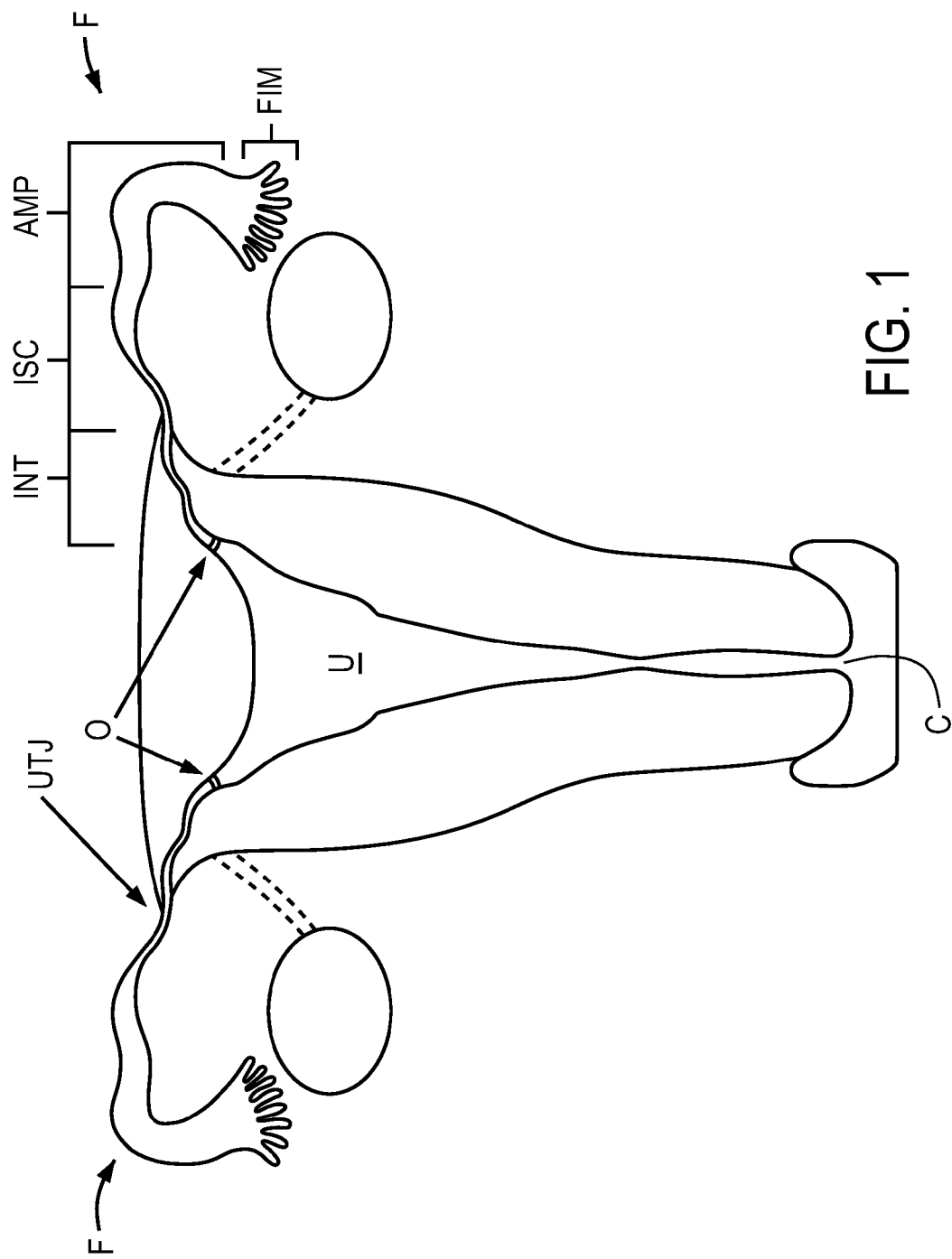
FIG. 1 is a schematic view illustrating the uterine and tubal anatomy for deployment of the contraceptive devices.

Contraceptive devices that provide substantially immediate and permanent sterilization are described herein. Systems and methods for transcervically delivering the contraceptive devices are also described herein. The contraceptive device may include an expandable implant. The implant includes hydrogel to provide substantially immediate sterilization, and tissue in-growth promoting agent or fibers to provide permanent sterilization. The hydrogel can provide immediate sterilization by swelling in a physiological environment once the device with hydrogel is deployed, and the tissue in-growth promoting agent (such as polyester fibers) promotes in-growth of tissue to permanently occlude the fallopian tube into which the device is implanted. As an alternative or in combination to hydrogel, the implant may include copper or cupric ions to provide substantially immediate sterilization. The implant may also include hydrogel to improve trackability (to provide ease of movement) of the implant through an ovarian pathway. The hydrogel can be formulated to be radiopaque (for X-ray visualization) or be visible under ultrasound imaging or MRI imaging.

Hydrogels may be formed from covalently or non-covalently crosslinked materials, and may be non-degradable ("biostable") in a physiological environment or broken down (biodegradable) by natural processes within the body, referred to as biodegradable or bioabsorbable. The breakdown process may be due to one of many factors in the physiological environment, such as enzymatic activity, heat, hydrolysis, or others, including a combination of these factors.

Hydrogels that are crosslinked may be crosslinked by any of a variety of linkages, which may be reversible or irreversible. Reversible linkages may be due to ionic interaction, hydrogen or dipole type interactions or the presence of covalent bonds. Covalent linkages for absorbable or degradable hydrogels may be chosen from any of a variety of linkages that are known to be unstable in an animal physiological environment due to the presence of bonds that break either by hydrolysis (e.g., as found in synthetic absorbable sutures), enzymatically degraded (e.g., as found in collagen or glycosamino glycans or carbohydrates), or those that are thermally labile (e.g., azo or peroxy linkages).

All of the hydrogel materials appropriate for use in the present invention should be physiologically acceptable and should be swollen in the presence of water. These characteristics allow the hydrogels to be introduced into the body in a "substantially deswollen" state and over a period of time hydrate to fill a void, a defect in tissue, or create a hydrogel-filled void within a tissue or organ by mechanically exerting a gentle force during expansion. The hydrogel may be pre-formed or formed in situ. The hydrogel can, in one embodiment, be made to be radiopaque by incorporating heavy metals or heavy metal compounds, such as barium sulfate, platinum, tungsten, gold, or iridium-based contrast material, into the hydrogel. The hydrogel can, in one embodiment, be made to be radiopaque by incorporating air/gas bubbles into the hydrogel; in some cases, the hydrogel will be inherently visible in ultrasound imaging modalities.

"Substantially deswollen" is defined as the state of a hydrogel wherein an increase in volume of the hydrogel of the article or device formed by such hydrogel is expected on introduction into the physiological environment. Thus, the hydrogel may be in a dry state, or less than equilibrium hydrated state, or may be partially swollen with a pharmaceutically acceptable fluid that is easily dispersed or is soluble in the physiological environment. The expansion process also may cause the implanted material to become firmly lodged within a hole, an incision, a puncture, or any defect in tissue which may be congenital, diseased, or iatrogenic in origin, occlude a tubular or hollow organ, or support or augment tissue or organs for some therapeutic purpose.

Hydrogels useful in practicing the present invention may be formed from natural, synthetic, or biosynthetic polymers. Natural polymers may include glycosminoglycans, polysaccharides, proteins etc. The term "glycosaminoglycan" is intended to encompass complex polysaccharides which are not biologically active (i.e., not compounds such as ligands or proteins) and have repeating units of either the same saccharide subunit or two different saccharide subunits. Some examples of glycosaminoglycans include dermatan sulfate, hyaluronic acid, the chondroitin sulfates, chitin, heparin, keratan sulfate, keratosulfate, and derivatives thereof.

In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust bean gum, arbinoglactan, pectin, amylopectin, gelatin, hydrophilic colloids such as carboxymethyl cellulose gum or alginate gum cross-linked with a polyol such as propylene glycol, and the like, also form hydrogels upon contact with aqueous surroundings.

Synthetic polymeric hydrogels generally swell or expand to a very high degree, usually exhibiting a 2 to 100-fold volume increase upon hydration from a substantially dry or dehydrated state. Synthetic hydrogels may be biostable or biodegradable or bioabsorbable. Biostable hydrophilic polymeric materials that form hydrogels useful for practicing the present invention include poly(hydroxyalkyl methacrylate), polyelectrolyte complexes), poly(vinylacetate) cross-linked with hydrolysable bonds, and water-swellable N-vinyl lactams.

Other suitable hydrogels include hydrophilic hydrogels know as CARBOPOL®, a registered trademark of B.F. Goodrich Co., Akron, Ohio, for acidic carboxy polymer (Carbomer resins are high molecular weight, allylpentaerythritol-crosslinked, acrylic acid-based polymers, modified with C10-C30 alkyl acrylates), polyacrylamides marketed under the CYANAMER® name, a registered trademark of Cytec Technology Corp., Wilmington, Del., polyacrylic acid marketed under the GOOD-RITE.® name, a registered trademark of B.F. Goodrich Co., Akron, Ohio, polyethylene oxide, starch graft copolymers, acrylate polymer marketed under the AQUA-KEEP® name, a registered trademark of Sumitomo Seika Chemicals Co., Japan, ester cross-linked polygtucan, and the like. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, and in Handbook of Common Polymers, (Scott & Roff, Eds.) Chemical Rubber Company, Cleveland, Ohio.

Hydrogels also may be formed to be responsive to changes in environmental factors, such as pH, temperature, ionic strength, charge, etc., by exhibiting a corresponding change in physical size or shape, so-called "smart" gels. For example, thermoreversible hydrogels, such as those formed of amorphous N-substituted acrylamides in water, undergo reversible gelation when heated or cooled about certain temperatures (lower critical solution temperature, LCST). Prevailing gel formation mechanisms include molecular clustering of amorphous polymers and selective crystallization of mixed phases of crystalline materials. Such gels, which are insoluble under physiological conditions, also advantageously may be used for practicing the present invention.

It is also possible to affect the rate at which a substantially dehydrated hydrogel rehydrates in a physiological environment, such as encountered upon implantation in an animal. For example, creating a porous structure within the hydrogel by incorporating a blowing agent during the formation of the hydrogel may lead to more rapid re-hydration due to the enhanced surface area available for the water front to diffuse into the hydrogel structure.

When a foamed gel is desired, a two component mixture of the precursors to a hydrogel forming system may be selected such that foaming and polymerization to form the hydrogel are initiated when the two fluid channels are mixed. A double barrel syringe assembly may be provided to mix the fluids, in which each barrel is equipped with a separate plunger to force the material contained therein out through a discharge opening. The plungers preferably are connected to one another at the proximal ends so that a force exerted on the plungers generates equal pressure within each barrel and displaces both plungers an equal distance.

The hydrogel forming precursors for the foregoing system may be selected so that, for example, a free radical polymerization is initiated when two components of a redox initiating system are brought together. One of these components additionally may include a foaming agent, e.g., sodium bicarbonate, that when exposed to an acidic environment (e.g., the other component in the syringe may comprise an acidic solution), releases carbon dioxide as a foaming agent. While the effervescent compound reacts with the water-soluble acid to release gases, the hydrogel structure is polymerizing and crosslinking, thereby causing the formation of a stable foamed gel. Alternatively, other techniques, which are per se known, may be used to foam the hydrogels.

In addition, the driving force for water to penetrate a dehydrated hydrogel also may be influenced by making the hydrogel hyperosmotic relative to the surrounding physiological fluids. Incorporation of charged species within hydrogels, for example, is known to greatly enhance the swellability of hydrogels. Thus the presence of carboxyl or sulfonic acid groups along polymeric chains within the hydrogel structure may be used to enhance both degree and rate of hydration. The surface to volume ratio of the implanted hydrogels also is expected to have an impact on the rate of swelling. For example, crushed dried hydrogel beads are expected to swell faster to the equilibrium water content state than a rod shaped implant of comparable volume.

Alternatively, instead of using dehydrated preformed hydrogels, in-situ formed hydrogels formed from aqueous solutions of precursor molecules also may be used. The hydrogels may be absorbable or biostable. The precursor solutions preferably are selected so that the hydrogels when formed in the physiological environment are below the equilibrium level of hydration. Thus, when formed in-situ, the hydrogels have the ability to hydrate and increase in size. If the hydrogels are formed in confined tissue spaces, the additional swelling is expected to further anchor the hydrogel in place.

Any of a variety of techniques may be used to form hydrogels in-situ. For example, monomers or macromers of hydrogel forming compositions may be further polymerized to form three dimensionally cross-linked hydrogels. The crosslinking may be covalent, ionic, and or physical in nature. Polymerization mechanisms permitting in-situ formation of hydrogels are per se known, and include, without limitation, free radical, condensation, anionic, or cationic polymerizations. The hydrogels also may be formed by reactions between nucleophilic and electrophilic functional groups, present on one or more polymeric species, that are added either simultaneously or sequentially. The formation of hydrogels also may be facilitated using external energy sources, such as in photoactivation, thermal activation and chemical activation techniques.

Absorbable polymers, often referred to as biodegradable polymers, have been used clinically in sutures and allied surgical augmentation devices to eliminate the need for a second surgical procedure to remove functionally equivalent non-absorbable devices. See, for example, U.S. Pat. No. 3,991,766 to Schmitt et al. and Shalaby, Encyclopedia of Pharmaceutical Technology (Boylan & Swarbrick, Eds.), Vol. 1, Dekker, N.Y., 1988, p. 465. Although these previously known devices were intended for repairing soft tissues, interest in using such transient systems, with or without biologically active components, in dental and orthopedic applications has grown significantly in the past few years. Applications of absorbable polymers are disclosed in Bhatia, et al., J. Biomater. Sci., Polym. Ed., 6(5):435 (1994), U.S. Pat. No. 5,198,220 to Damani, U.S. Pat. No. 5,171,148 to Wasserman, et. al., and U.S. Pat. No. 3,991,766 to Schmitt et al.

Synthesis and biomedical and pharmaceutical applications of absorbable or biodegradable hydrogels based on covalently crosslinked networks comprising polypeptide or polyester components as the enzymatically or hydrolytically labile components, respectively, have been described by a number of researchers. See, e.g., Jarrett et al., "Bioabsorbable Hydrogel Tissue Barrier: In Situ Gelation Kinetics," Trans. Soc. Biomater., Vol. XVIII, 182 (1995); Sawhney et al., "Bioerodible Hydrogels Based on Photopolymerized Poly(ethyleneglycol)-co-poly(.alpha.-hydroxy acid) Diacrylate Macromers", Macromolecules, 26:581-587 (1993); Park, et al., Biodegradable Hydrogels for Drug Delivery, Technomic Pub. Co., Lancaster, Pa. (1993); Park. "Enzyme-digestible swelling hydrogels as platforms for long-term oral delivery: synthesis and characterization," Biomaterials, 9:435-441 (1988). The hydrogels most often cited in the literature are those made of water-soluble polymers, such as polyvinyl pyrrolidone, which have been crosslinked with naturally derived biodegradable components such as those based on albumin.

Totally synthetic hydrogels have been studied for controlled drug release and membranes for the treatment of post-surgical adhesion. Those hydrogels are based on covalent networks formed by the addition polymerization of acrylic-terminated, water-soluble polymers that have at least one biodegradable spacer group separating the water soluble segments from the crosslinkable segments, so that the polymerized hydrogels degrade in vivo. Such hydrogels are described in U.S. Pat. No. 5,410,016, which is incorporated herein by reference, and may be particularly useful for practicing the present invention.

Hydrogels for use in the present invention may be formed by the polymerization of macromers that form hydrogel compositions that are absorbable in vivo. These macromers, for example, may be selected from compositions that are biodegradable, polymerizable, and substantially water soluble macromers comprising at least one water soluble region, at least one degradable region, and statistically more than 1 polymerizable region on average per macromer chain, wherein the polymerizable regions are separated from each other by at least one degradable region.

Hydrogels that have some mechanical integrity and that cannot be "extruded" from the implantation site by forces applied by natural movement of surrounding tissues are preferred for this invention. Thus, hydrogels suitable for use in the present invention preferably are physically or chemically crosslinked, so that they possess some level of mechanical integrity even when fully hydrated. The mechanical integrity of the hydrogels may be characterized by the tensile modulus at breaking for the particular hydrogel. Hydrogels having a tensile strength in excess of 10 KPa are preferred, and hydrogels having a tensile strength greater than 50 KPa are more preferred.

In one embodiment, a hydrogel for use with any of the fallopian tube implants described herein can be created from a mixture of a solution containing sodium metaborate (or "Borax") and a solution containing polyvinyl alcohol (PVA). Each of these two solutions is first separately prepared and then mixed together to create a hydrogel which can be applied as a liquid (which is gelling), onto a fallopian tube implant (or a set of implants). The liquid dries onto the implant to create the dried (deswollen) hydrogel which will swell after being introduced into a fallopian tube. The swollen hydrogel can fully and/or functionally occlude the fallopian tube at least until the tissue ingrowth promoting agent has caused sufficient tissue ingrowth into the fallopian tube to occlude the tube. The mixture of the two solutions can be applied repeatedly onto the implant to build up, over time, a hydrogel component on the implant; for example, a few drops of the mixture can be applied to an implant and allowed to dry (e.g. with the aid of heated air, such as air from a conventional hair dryer, etc.) and then further drops of the mixture are applied to the dried hydrogel on the implant to build up the structure of the hydrogel on the implant. This mixture may be created from a variety of different formulations such as the following different formulations, shown in the following table.

A procedure for creating the mixture of formulation "1" will now be described. Add 100 ml of water to a first beaker and 200 ml of water to a second beaker and place each beaker on its own hot plate (with integrated magnetic stirrer); set heat at 80° C. and place a magnet stirrer in each beaker. Set stirrer speed to at least 300 rpm; this speed should be increased as the ingredients are added to their beakers. Add 4.0 gm of borax into the first beaker (which contains 100 ml of water), and add 4 gm of PVA into the 200 ml of water in the second beaker. Allow the ingredients in each beaker to fully dissolve into solution. Pour 100 ml of the PVA solution from the second beaker into an empty third beaker and pour 7 ml of the borax solution from the first beaker into the third beaker and stir the mixture in the third beaker. A thick hydrogel material begins to form in the mixture in the third beaker; slowly pour 50 ml of water (at room temperature) in the third beaker and continue to stir the mixture to assure that all water is making contact with the hydrogel. The mixture can then be applied to an implant to add hydrogel to the implant, such as the implant 150.

Another type of hydrogel can be formed from a molded mixture of Polyethylene Oxide (PEO) and Triallyl Isocyanurate (TI). This mixture is molded in a mold into which an implant (e.g. any one of the implants shown or described herein) is placed along with both the PEO and the TI. The mold forms, through a high temperature and high pressure process, a hydrogel on the implant. In one embodiment, the PEO and IT are mixed together, as powders, in a conventional tumble mixer and then added, as a mixed powder to the mold (and the implant is also placed into the mold), In one embodiment, 100 gm of PEO is mixed with about 0.25 to 0.8 gm of TI and this mixture is mixed in a tumble mixer and then molded, in a mold with an implant in the mold, at a temperature and pressure sufficient to melt both powders and to form a hydrogel bonded to the implant in the mold.

In certain embodiments, a hydrogel from Hydromer Incorporated of Branchburg, N.J. may be used as a hydrogel applied to any of the fallopian tube implants described herein.

Referring now to FIG. 1, access to a uterus U is gained through the cervix C. From within the uterus U, the fallopian tubes F are accessed via the tubal ostiums O. The fallopian tubes F generally include three segments between the ostium O and the fimbria FIM. Beginning adjacent the uterus U, the intramural segment INT of the fallopian tubes F are surrounded by the muscular uterine tissues. Beginning at the uterotubal junction UTJ, the fallopian tubes F extend beyond the uterine tissues and within the peritoneal cavity along an isthmic segment ISC, and then along an ampullary segment AMP.

| Formulation | First Solution | Second Solution | Mixture |
| --- | --- | --- | --- |
| 1 | 4 gm of borax in 100 ml of water | 4 gm of PVA in 200 ml of water | 7 ml of first solution and 100 ml of second solution |
| 2 | 4 gm of borax in 100 ml of water | 1 gm of PVA in 100 ml of water | 1.75 ml of first solution and 7.5 ml of second solution |
| 3 | 4 gm of borax in 100 ml of water | 1 gm of PVA in 100 ml of water | 1 ml of first solution and 9 ml of second solution |
| 4 | 4 gm of borax in 100 ml of water | 1.2 gm of PVA in 100 ml of water | 1.5 ml of first solution and 9 ml of second solution |
| 5 | 4 gm of borax in 100 ml of water | 4 gm of PVA in 100 ml of water | 4 ml of first solution and 50 ml of second solution, then diluted with 60-80 ml of water |
| 6 | 4 gm of borax in 100 ml of water | 1.3 gm of PVA in 100 ml of water | 1.5 ml of first solution and 25 ml of second solution |

Figure 2A:
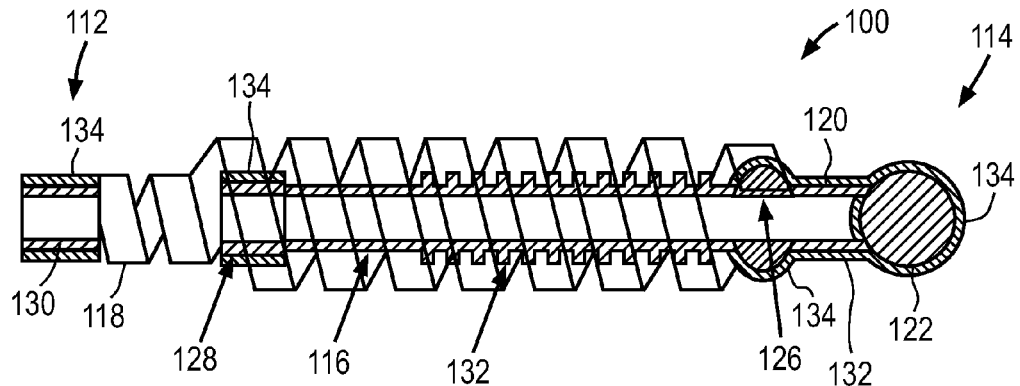
FIGS. 2A-2B illustrate a contraceptive device in accordance with one embodiment of the invention.
Figure 2B:
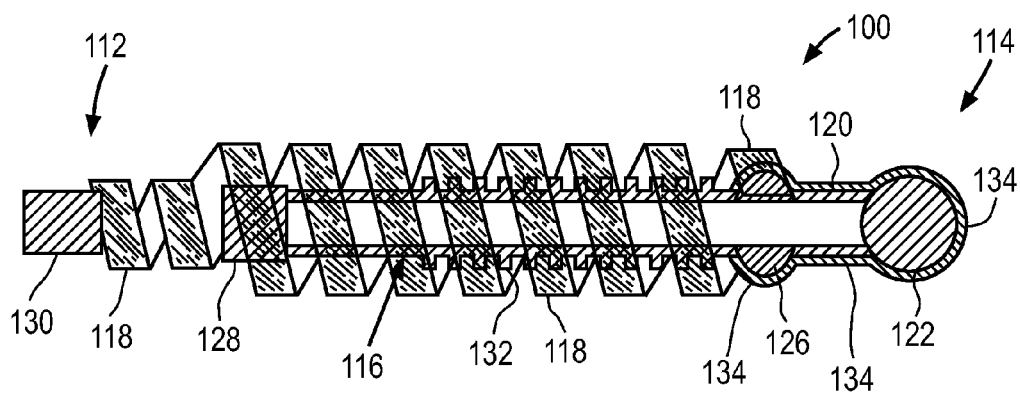
Figure 3:
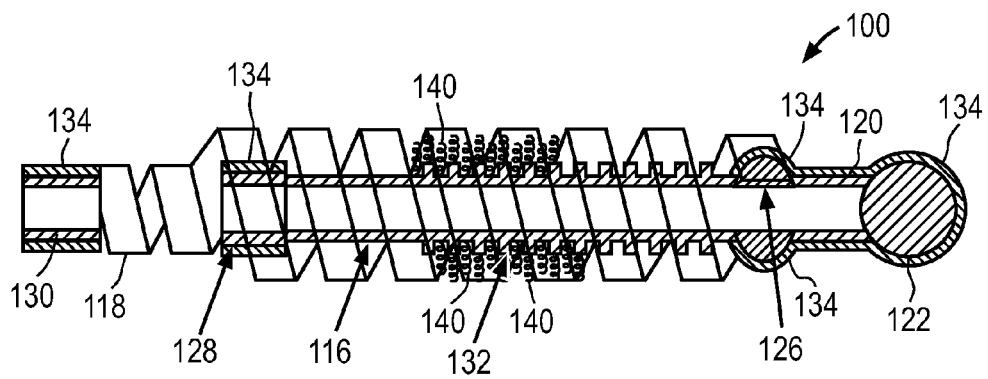
FIGS. 3, 3A-3I illustrate a contraceptive device in accordance with one embodiment of the invention.

FIGS. 2A, 2B and FIG. 3 illustrate an exemplary expandable implant. FIG. 2A illustrates an implant formed entirely of a polymer or metallic material, while FIG. 2B illustrates the implant formed partially of a polymer material and partially of a metallic material.

The expandable implant may be formed from metal such as stainless steel or a superelastic or shape memory material such as a nickel titanium (NiTi) alloy such as nitinol, or platinum, or tantalum, or gold, or rigid or semi-rigid biocompatible plastics. In one particular embodiment, the expandable implant may be formed at least in part from a superelastic material providing a controlled force on the body lumen such as a portion of the fallopian tube during expansion of the implant. The implant may self-expand radially from a first diameter to a second diameter which is larger than the first diameter. The implant may be delivered by a delivery system (e.g. a delivery catheter) which constrains the implant to the size of the first diameter and after the implant is deployed, it may expand to the second diameter which at least slightly exceeds the diameter of a lumen of the fallopian tube. The material or materials of the implant may be superelastic so that the implant can expand in a manner that causes it to resiliently apply an anchoring force against the wall of the fallopian tube, thereby resisting against being expelled by the fallopian tube.

As shown in FIGS. 2A-3, the expandable implant 100 has a proximal end 112 and a distal end 114. The expandable implant 100 also includes an inner member 116 and an outer coil 118. The inner member 116 includes a tip 120 which may be atraumatic and which is designed to be arranged at a distal end of the implant 100. The tip 120 includes a ball 122 at the distal end of the implant 100. The implant 100 includes a distal attachment 126 at its distal end which couples the inner member 116, outer coil 118 and tip 120. The implant 100 also includes an end piece 130 which is attached to a proximal end of the outer coil. The implant 100 also includes a proximal attachment 128 that releasably couples the outer coil 118 with the inner member 116 through the end piece 130. The attachments 126, 128 may be formed by soldering or molding operations in one or more dies.

The illustrated inner member includes optional teeth 132; these teeth are designed to, in one embodiment, engage a meshlike material 140 such as polyester fibers or other fibers or furs which are designed to promote a tissue ingrowth into and around the implant 100 and which are one embodiment of a tissue ingrowth promoting agent, as shown in FIG. 3. The tissue ingrowth promoting agent 140 is disposed between the outer coil 118 and the inner member 116.

The surface of the implant may be designed to facilitate epithelial growth; one way of doing this is to provide the implant with an open or latticelike framework to promote and support epithelial growth into as well as around the implant to ensure secure attachment to an embodiment within the wall of the body lumen. The implant may include a tissue ingrowth promoting agent such as a polyester fiber (e.g. polyethylene terephthalate) or other materials known to facilitate fibrotic or epithelial growth. The surface of the implant may also be modified or treated or include such a tissue ingrowth promoting material. The surface modification may include plasma deposition or laser drilling or photochemical etching or sintering and the like. Further, increasing the surface area of the implant by such surface modification techniques (e.g. surface drilling or etching or sintering) can also provide greater adhesion for the epithelial tissue. Suitable surface treatments include plasma etching, sandblasting, machining and other treatments to roughen the surface. In other embodiments, the implant may be coated or seeded to spur epithelialization. For example, the implant can be coated with a polymer having impregnated therein a drug, enzyme or protein for inducing or promoting epithelial tissue growth. Any of these various techniques for including a tissue ingrowth promoting agent may be used with the various other implants shown or described herein.

As described above, hydrogel 134 is also provided on the implant. For example, in FIGS. 2A and 3, the hydrogel 134 is provided on the distal ball 122, tip 120, distal attachment 126, proximal attachment 128 and end piece 130. In FIGS. 2A and 3, the hydrogel is provided on the implant by coating each of the distal ball 122, tip 120, distal attachment 126, proximal attachment 128 and end piece 130 with hydrogel (which after the coating preferably obtains a de-swollen state).

Figure 3A:
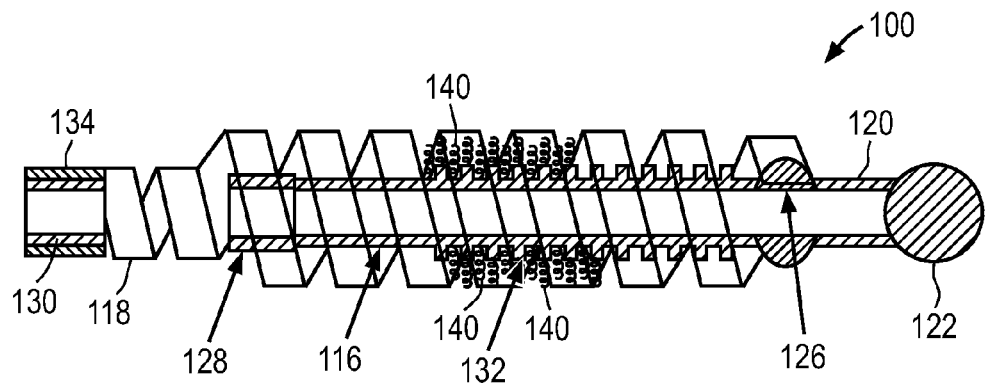
Figure 3B:
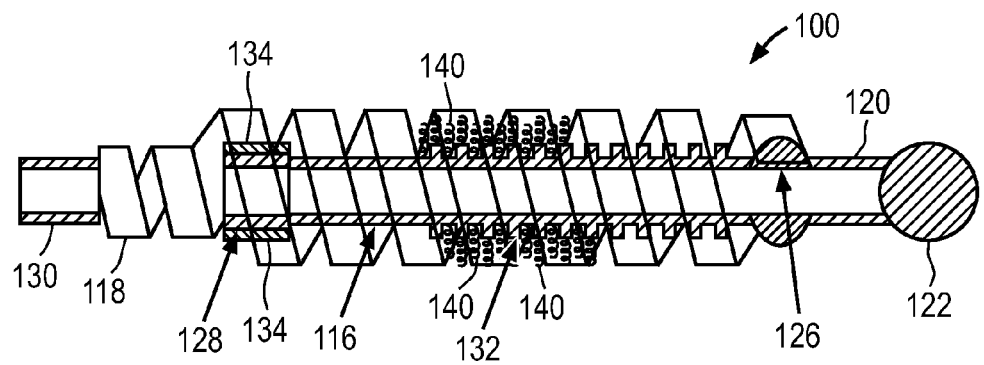
Figure 3C:
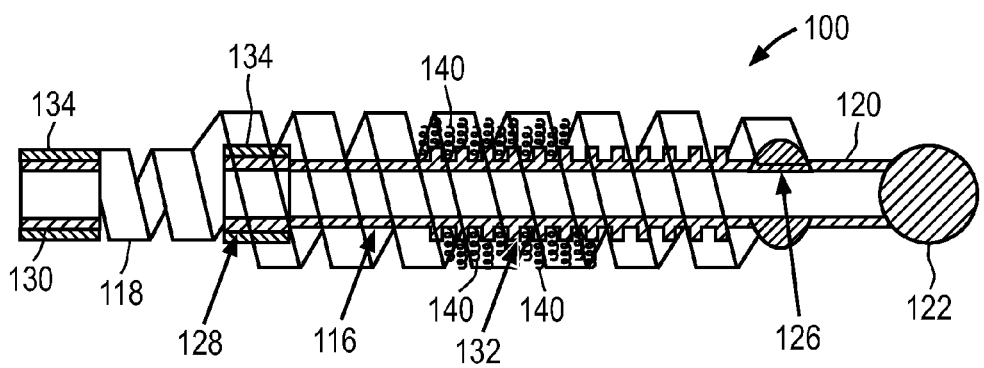
Figure 3D:
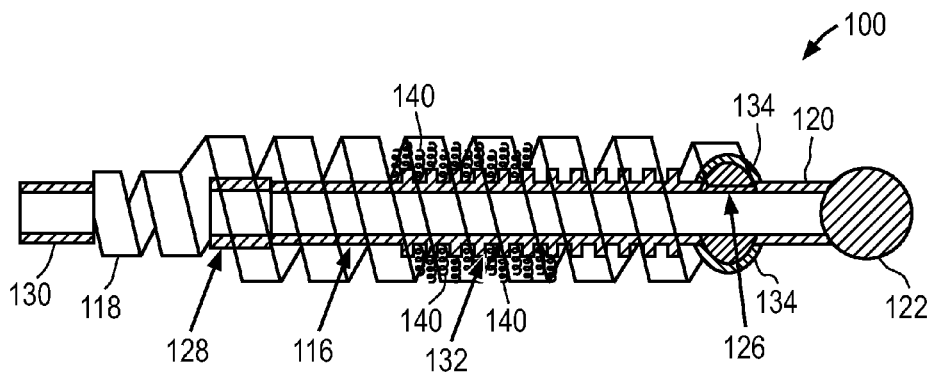
Figure 3E:
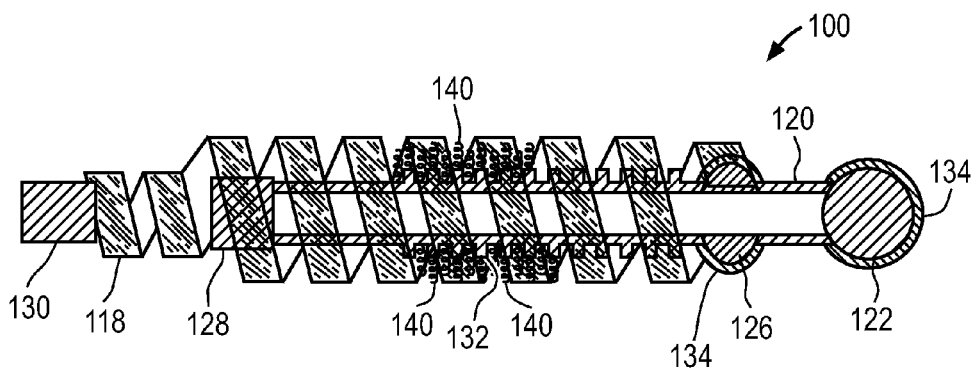
Figure 3F:
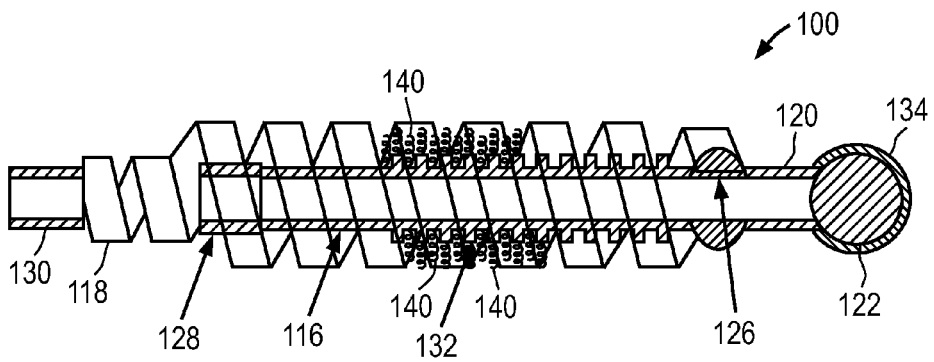

However, the hydrogel need not be provided on each of the distal ball 122, tip 120, distal attachment 126, proximal attachment 128 and end piece 130. For example, as shown in FIG. 2B, the hydrogel 134 is applied to the distal ball 122, tip 120 and the distal attachment 126 but not to the rest of the implant; as shown in FIG. 3A, the hydrogel 134 is a coating provided on only the end piece 130. In another embodiment, as shown in FIG. 3B, the hydrogel 134 is a coating provided only on the proximal attachment 128. In another embodiment, as shown in FIG. 3C, the hydrogel 134 is a coating provided on both the proximal attachment 128 and the end piece 130. In another embodiment, as shown in FIG. 3D, a hydrogel coating 134 is provided on the distal attachment 126. In another embodiment, as shown in FIG. 3E, a hydrogel coating 134 is provided on the distal attachment 126 and the distal ball 122. In another embodiment, as shown in FIG. 3F, a hydrogel coating 134 is provided only on the distal ball 122. It will be appreciated that other combinations of coatings may be provided; the above description was merely exemplary.

Figure 3G:
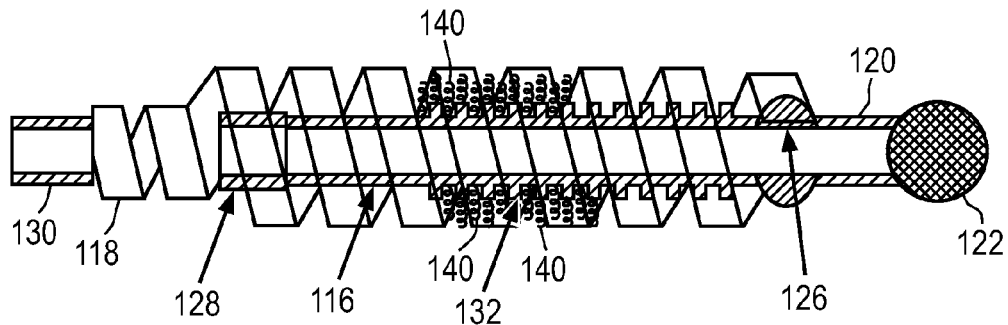
Figure 3H:
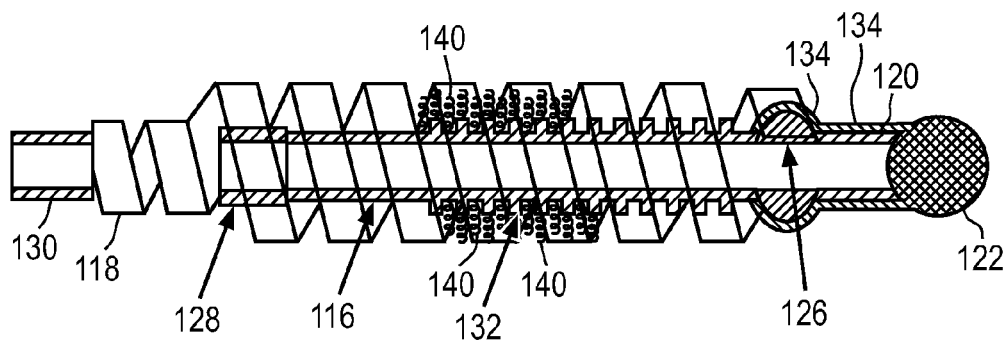
Figure 3I:
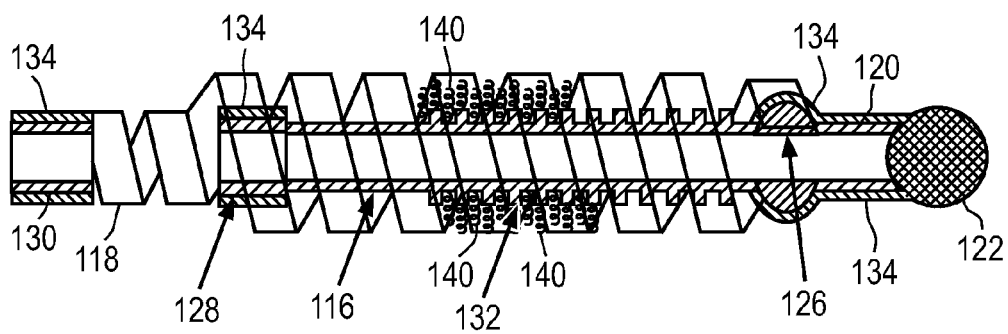

In the embodiments described above, the hydrogel is provided as a coating. As an alternative or in combination with the hydrogel coating, a portion of the implant 100 may be made of hydrogel. For example, as shown in FIG. 3G, the distal ball 122 is made entirely of hydrogel. In another embodiment, as shown in FIG. 3H, the distal ball 122 is made of hydrogel and the distal tip 120 and distal attachment 126 are both coated with hydrogel 134. In another embodiment, as shown in FIG. 3I, the distal ball 122 is made of hydrogel, and the distal tip 120, distal attachment 126, proximal attachment 128 and end piece 130 are coated with hydrogel 134. It will be appreciated that other portions of the implant 100 may be formed of hydrogel as well. The distal ball 122 may be formed from hydrogel by, for example, molding the hydrogel around the tip 120. Alternatively, a hydrogel plug may be attached (e.g., adhered, affixed) to the tip 120.

Alternatively or in combination with the hydrogel, the distal ball 122 or other components of the implant 100 may be made of copper or be coated with a cupric ion containing polymer. Alternatively, the hydrogel may include cupric ions. The copper reacts to form cupric ions when implanted in a patient's body, or the cupric ions disperse to provide substantially immediate sterilization.

Figure 4B:
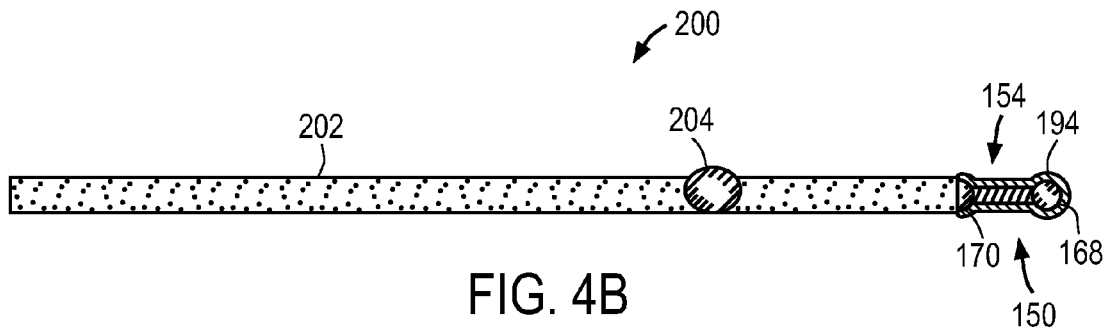
FIGS. 4B-4E illustrate a contraceptive device and delivery system in accordance with one embodiment of the invention.
Figure 4C:
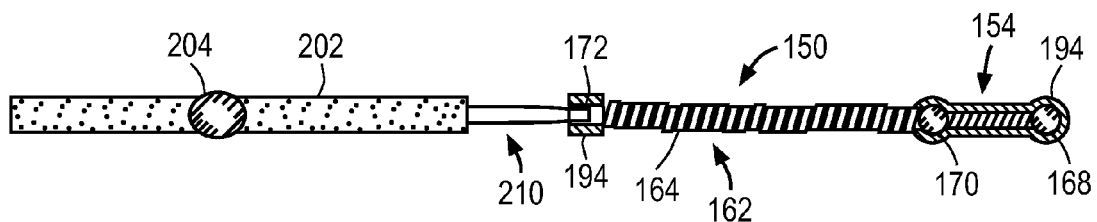
Figure 4A:
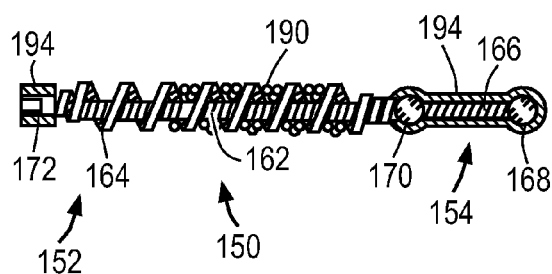
FIG. 4A illustrates a contraceptive device in an expanded position in accordance with one embodiment of the invention.

FIG. 4A illustrates another implant 150 that can be used in accordance with one embodiment of the invention. The implant 150 has a proximal end 152 and a distal end 154. The implant 150 includes an inner coil 162, an outer coil 164 and a flexible tip 166 having a distal ball 168. The implant 150 also includes a distal attachment 170 connecting the inner coil 162, outer coil 164 and flexible tip 166. An end piece 172 is provided at the proximal end 152 of the implant 150. The end piece 172 releasably couples the implant 150 to a release catheter (e.g. a delivery wire) and attaches the inner coil 162 and outer coil 164 at their proximal ends until the implant is to be expanded. The flexible tip 166 may have a slight (e.g. 15 degree), preformed bend.

The implant 150 may also include a tissue ingrowth promoting agent 190, which is secured to the inner coil 162 or to the outer coil 164. The tissue ingrowth promoting agent may be a polyester fiber or other types of agents designed to cause tissue ingrowth to functionally occlude the fallopian tube.

The contraceptive device 150 resembles the Essure device from Conceptus, Inc. of Mountain View, Calif., in that there is an outer coil which may be formed from a superelastic or resilient member and an inner coil which is coupled to the outer coil. The outer coil is designed to radially expand (e.g. through self expansion after it is deployed) to engage the walls of a portion of the fallopian tube to thereby engage those walls and hold the device within the fallopian tube.

Hydrogel 194 may also be provided on the implant 150. The hydrogel 194 may be a coating or a component of the implant 150 and may be formed as described above. In FIG. 4A, each of the distal ball 168, flexible tip 166, distal attachment 170 and end piece 172 are coated in hydrogel 194. It will be appreciated, however, that variations to the coatings may be made as described above with reference to FIGS. 3-3I. Furthermore, as described above, as an alternative to or in combination with the hydrogel, the implant 150 may include copper and/or cupric ions.

The implant 150 (or implant 100) is delivered to a fallopian system using a delivery system, such as the delivery system 200 shown in FIGS. 4B-4E. The delivery system 200 includes a delivery catheter 202 and a marker 204 disposed on the delivery catheter 202. The marker 204 may be one or more of the various types of conventional markers such as an optically visible marker (e.g. a marker which is colored to distinguish from its surroundings) which is visible during a hysteroscopy by visible light and a camera or a radiopaque marker or an ultrasound marker (which is visible in an ultrasound image) or other known markers. In FIG. 4B, the distal portion 154 of the contraceptive device 150 is shown.

FIG. 4C shows the implant 150 after the delivery catheter 202 has been retracted (or alternatively, the contraceptive device has been pushed relative to the delivery catheter) such that the implant 100 is fully viewable. The end piece 172 of the implant 150 is adjacent to and abuts a release catheter 210. The release catheter 210 may include a pin or other interface designed to mate with a receptor or other interface on the end piece 172 to thereby releasably couple the contraceptive device 150 to the release catheter 210. In one exemplary embodiment, the two interface elements on the release catheter 210 and the end piece 172 are coupled through an interference fit or a friction fit or a screw fit. The contraceptive device and the release catheter can, in one embodiment, be released by retracting the release catheter. In another exemplary embodiment, the two interface elements on the release catheter 210 and the end piece 172 may resemble a screw and a nut which more securely secures the contraceptive device and release catheter to each other. The contraceptive device and release catheter can be released by unscrewing the contraceptive device from the release catheter after the contraceptive device has been implanted. The expanded contraceptive device resembles the implant as shown in FIG. 4A.

Figure 4D:
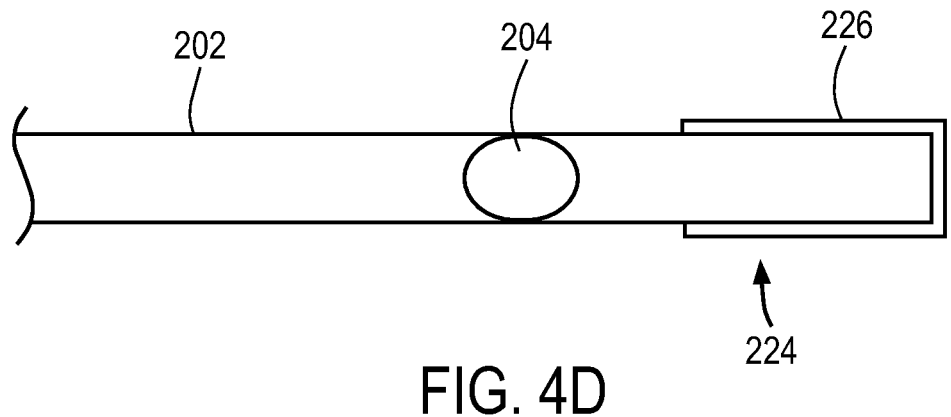

FIG. 4D shows an alternative embodiment of the delivery catheter 202. In one embodiment, the sheath of the delivery catheter 202 is substantially coated in a hydrophilic coating (not shown) to minimize friction, while the distal end 224 of the delivery catheter 202 is coated with a hydrophobic coating 226 to prevent the hydrogel, on the implant, from swelling before the implant 150 is delivered to the fallopian tube. The distal end of the implant 150 may extend, in one embodiment, beyond the distal end of the sheath during delivery (but before release of the implant) and hence the coating can protect the implant, during delivery, from saline even though the implant extends beyond the end of the sheath during delivery. Any suitable material that is compatible for use in medical or therapeutic applications may be used for the hydrophobic coating. Such materials include, without limitation. TEFLON, silicones, parylene, and the like. As shown in FIG. 4D, the hydrophobic coating 226 encapsulates the distal end of the delivery catheter and prevents saline from entering the distal end, and hence the coating 226 protects the hydrogel on the implant from the surrounding saline environment until the coating 226 is pierced, dissolved or removed. The implant (e.g., implant 150 or implant 100) is surrounded by and encapsulated by the sheath of the delivery catheter and is therefore not exposed to a physiological environment of a fallopian tube until the hydrophobic coating 226 is pierced, dissolved or removed. In one embodiment, the hydrophobic coating 226 may be rapidly bioabsorbable or biodegradable within a physiological environment, and hence it will naturally dissolve in the presence of a physiological environment. In another embodiment, the coating 226 can be pierced by retracting the sheath of the delivery catheter (while the implant within the sheath is held stationary and pushes through the coating 226) or by pushing the implant through the sheath (or by a combination of retracting proximally the sheath while pushing distally the implant). In another embodiment, the coating 226 can be a hydrophilic coating which can be pierced or dissolved or removed; for example, it can be a hydrophilic coating that is rapidly biodegradable or bioabsorbable in a physiological environment within a fallopian tube. In another embodiment, a coating, such coating 226 can encapsulate the entire implant at both proximal and distal ends of the implant d no sheath is needed; this coating can be biodegradable or bioabsorbable and allow for the delivery catheter to deliver the implant without a sheath.

Figure 4E:
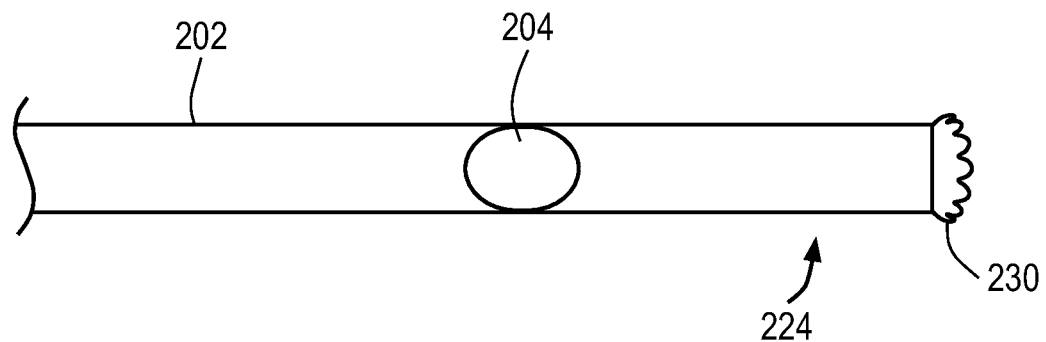

FIG. 4E shows another embodiment of the delivery catheter 202 in which a hydrophobic membrane 230 is provided over the distal end 224 of the delivery catheter 202. The hydrophobic membrane 230 similarly prevents the hydrogel from swelling before the implant 150 is delivered to the fallopian tube. The membrane 230 may be pierceable, dissolvable or removable such that the implant 150 can be delivered through the distal end of the delivery catheter 202.

Figure 5A:
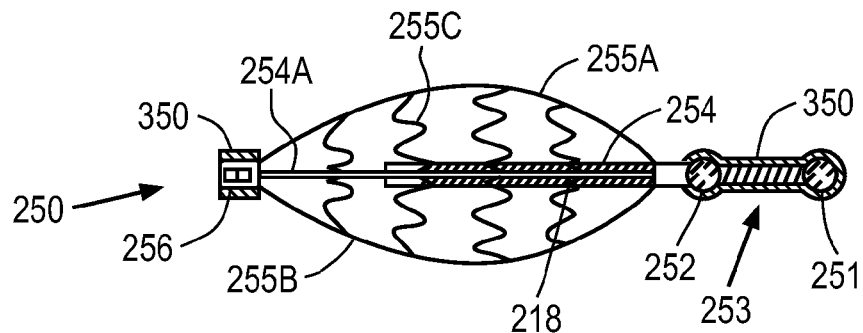
FIGS. 5A-5E illustrate a contraceptive device in accordance with one embodiment of the invention.

FIGS. 5A-5E show alternative embodiments of implants, which may include hydrogel as described above. The implant 250 of FIG. 5A includes a tip 251 near the distal portion 253 and also includes an attachment 252 which couples the distal end of top and bottom members 255A and 255B to the implant 250. Hydrogel 350 is applied, as a coating in one embodiment, to the distal portion 253 and to the end piece 256. The proximal ends of these members are coupled to end piece 256 which is also coupled to an inner frame 254A which is coupled to the core 254. An inner mesh 255C is coupled to and extends from each of the members to the inner core 254 and to the inner frame 254A as shown in FIG. 5A. The inner mesh may be formed from the same material as the top and bottom members or may be formed from a tissue ingrowth promoting agent.

Figure 5B:
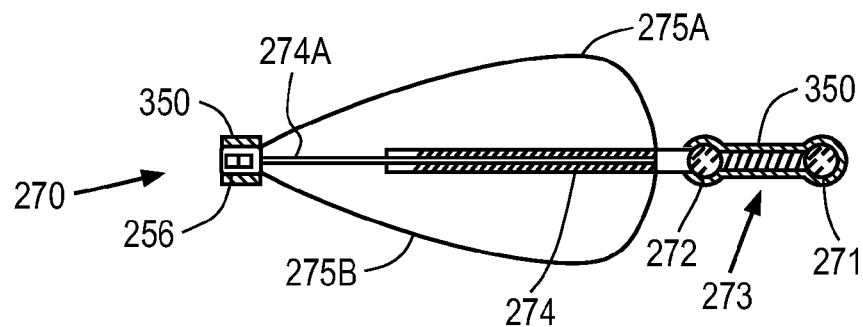

FIG. 5B shows an implant 270 which includes a tip 271 at a distal portion 273 and an attachment 272 which attaches the top and bottom members 275A and 275B to the core 274. The core 274 is attached to an inner frame 274A which is in turn attached to an end piece 276. The proximal ends of the top and bottom members 275A and 275B are attached to the end piece 276 as shown in FIG. 5B. The top and bottom members 275A and 275B may be formed from a material such as a superelastic or shape memory material which radially expands from a contracted state to an enlarged state similar. This is also true of the top member 255A and the bottom member 255B shown in FIG. 5A, as well as the other top and bottom members shown in FIGS. 5C, 5D and 5E.

Figure 5C:
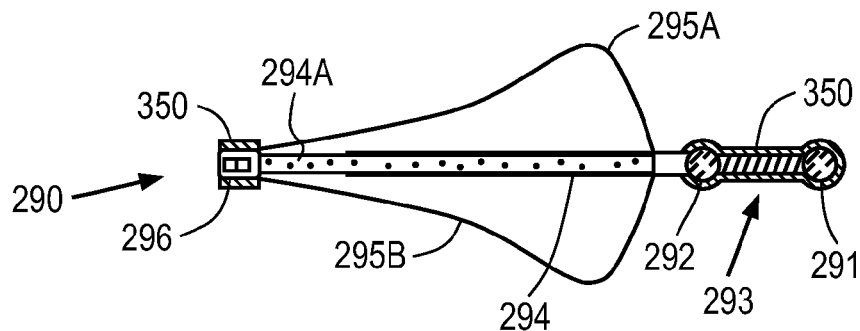

FIG. 5C shows an implant 290 which includes a tip 291 near a distal portion 293 which in turn is coupled to an attachment 292 which attaches the top and bottom members 295A and 295B to the core 294 as shown in FIG. 5C. An inner frame 294A which is coupled to the core 294 is coupled at its proximal end to an end piece 296 which in turn is coupled to the proximal ends of the top and bottom members 295A and 295B.

Figure 5D:
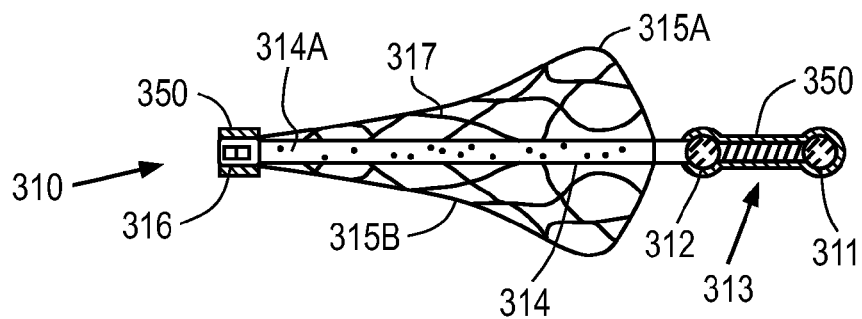

FIG. 5D shows an implant 310 which includes a tip 311 near a distal portion 313. An attachment 312 is coupled to the distal portion 313 and is also coupled to the distal ends of the top and bottom members 315A and 315B. A core 314 is also coupled to the attachment 312, and an inner frame 314A is coupled to the core 314. The proximal portion of the inner frame 314A is coupled to an end piece 316. The end piece 316 is coupled to a proximal end of each of the top and bottom members 315A and 315B. An inner mesh 317, which is similar to the mesh 255C of FIG. 5A, is coupled between the top and bottom members and the core 314 and the inner frame 314A. The inner frame 314A may be the same component as the distal portion 313.

Figure 5E:
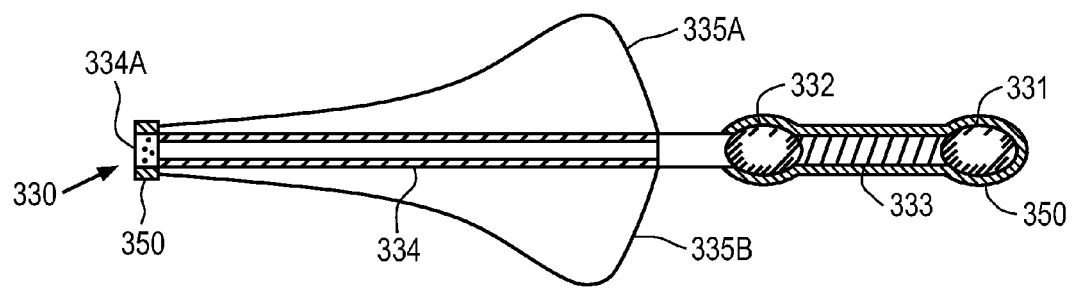

FIG. 5E shows an alternative embodiment of another implant in which the top and bottom members are secured only to the attachment 332 and not to the end piece 334A which is at the proximal end of the core 334. The implant 330 of FIG. 5E also includes a tip 331 which is coupled to a distal portion 333 which is in turn coupled to an attachment 332. The core 334 may, in an alternative embodiment, be the same component as the distal portion 333. The distal ends of the top and bottom members 335A and 335B are coupled to the attachment 332. The designs shown in FIGS. 5A-5E may be formed from multiple pieces which are brought together or may be formed as one piece.

Hydrogel 350 may also be provided on any one of the implants 250, 270, 290, 310 or 330. The hydrogel 350 may be a coating or a component of implants 250, 270, 290, 310 or 330 may be formed of hydrogel, as described above. It will be appreciated that variations to the coatings of the implants 250, 270, 290, 310 or 330 may be made as described above with reference to FIGS. 3-3I. Furthermore, as described above, as an alternative to or in combination with the hydrogel, any one of the implants 250, 270, 290, 310 or 330 may include copper and/or cupric ions. In addition, any one of the implants 250, 270, 290, 310, or 330 may include a tissue ingrowth promoting agent as described herein.

Figure 6A:
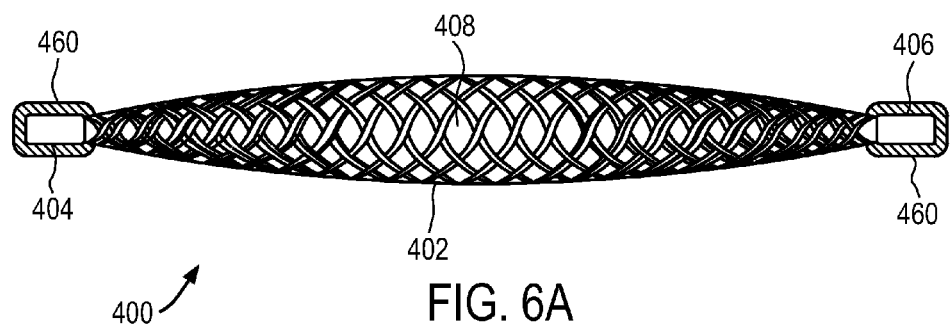
FIGS. 6A-6C illustrate a contraceptive device in accordance with one embodiment of the invention.

FIG. 6A shows a top view of one particular exemplary implant 400 which resembles a braided stent that has a frame 402 which surrounds an inner portion 408 which may be hollow or may be filled with a mesh or other tissue ingrowth promoting agents. The ends of the frame 402 are capped by ends 404 and 406 as shown in FIG. 6A. In an alternative embodiment of the implant 400, the ends of the frame 402 are opened and are not capped.

Figure 6B:
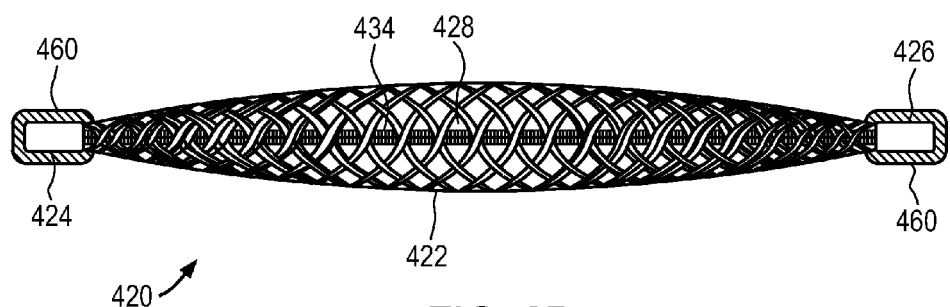

FIG. 6B shows a top view of another exemplary implant 420 which is similar to implant 400 except that implant 420 includes an inner member (e.g. a coil 434) which is surrounded by the braided frame 422 and which is attached to ends 424 and 426. The coil 434 is disposed within the open, hollow inner portion 428 which is also surrounded by the braided frame 422. The open, hollow inner portion 428 may include a tissue ingrowth promoting agent such as a polyester fiber or fibers (e.g. polyethylene terephthalate) or other materials known to facilitate fibrotic or epithelial growth.

Figure 6C:
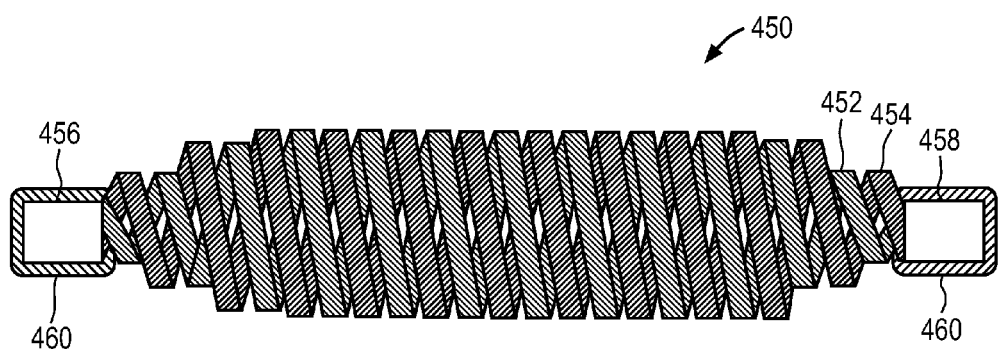

FIG. 6C shows a top view of another exemplary implant 450 which includes two coils 452 and 454 which are each attached to end 458 on one side (e.g. a distal end) of implant 450 and which are each attached to end 456 on the other side (e.g. a proximal end) of implant 450. An open, hollow inner portion is contained within the space defined by the two coils 452 and 454. This open, hollow inner portion may optionally include a tissue ingrowth promoting agent (e.g. polyester fibers) and it may further optionally include an inner member (e.g. a coil, not shown, which resembles coil 434) which is surrounded by the two coils 452 and 454. The implant 450 may be designed so that a compressive force on one end of the implant 450 causes the other end to expand. This will tend to provide an anchoring force against the wall of a fallopian tube at least at one point of the implant 450. In the case of implants 400, 420 and 450, as well as the other implants described and/or shown herein, the tissue ingrowth promoting agents may be placed within the implant or on the exterior of the implant or both within and on the exterior of the implant. These agents may extend longitudinally and/or traversely to the implants. A further description of aspects of the various implants shown in FIGS. 2A, 2B, 3, 3A-3I, 5A-5E and 6A-6C is provided in U.S. Patent Application Publication No. 2005/0274384 which is incorporated herein by reference.

Hydrogel 460 may also be provided on any one of the implants 400, 420 or 450. The hydrogel 460 may be a coating or a component of any one of the implants 400, 420 or 450 may be formed of hydrogel, as described above. It will be appreciated that variations to the coatings may be made as described above with reference to FIGS. 3-3I. Furthermore, as described above, as an alternative to or in combination with the hydrogel, any one of the implants 400, 420 or 450 may include copper and/or cupric ions. In addition, any one of the implants 400, 420 or 450 may include a tissue ingrowth agent as described herein.

FIGS. 7A-G illustrate a method of delivering the contraceptive device to a fallopian tube and facilitating substantially immediate and permanent sterilization. FIGS. 7A-7G illustrate delivery of implant 150; however, other implants described herein may be delivered in a similar manner. Variations as known to those of skill in the art may need to be made for some of the implants described above.

Figure 7A:
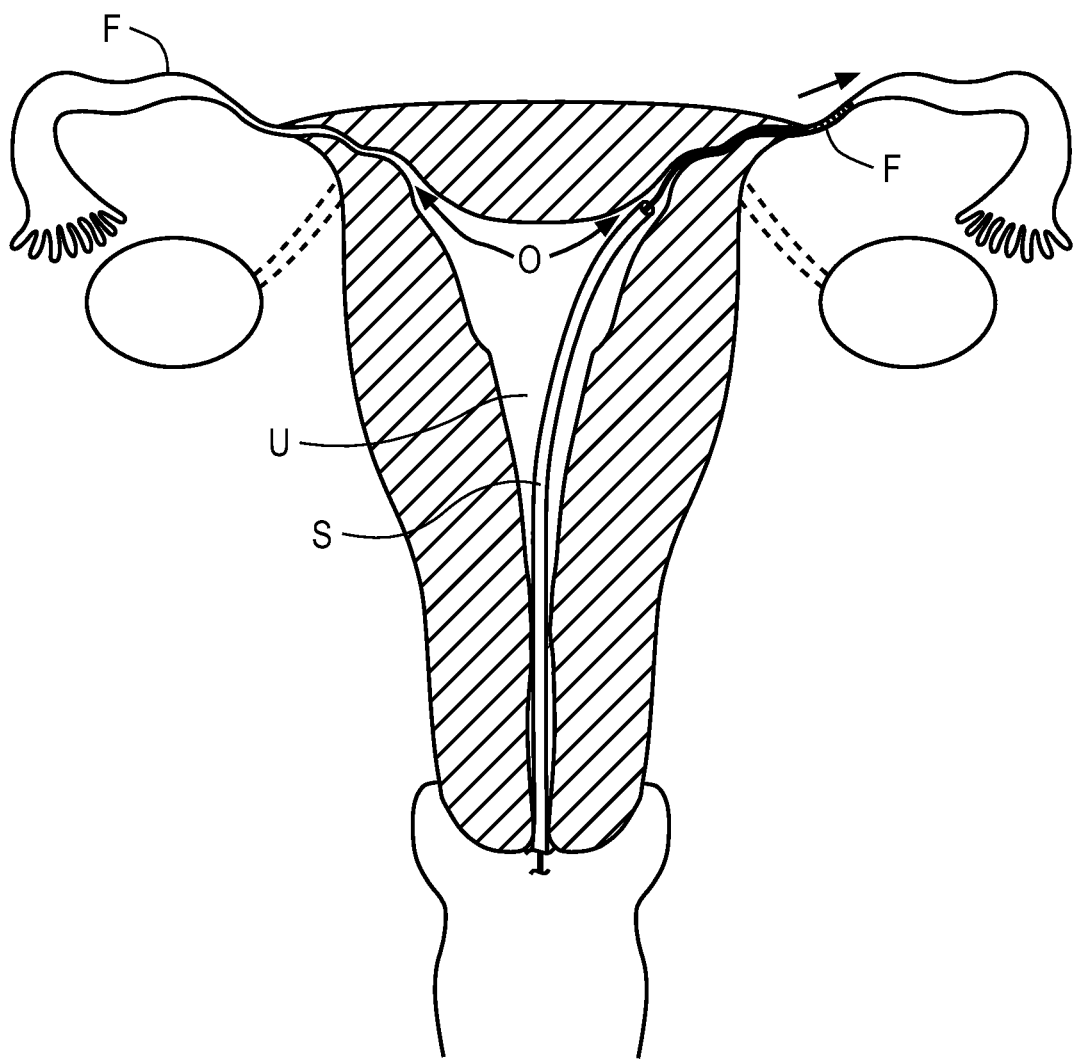
FIGS. 7A-7G illustrate delivery of a contraceptive device in accordance with one embodiment of the invention.

Referring now to FIG. 7A, a delivery system S, such as delivery system 200 is introduced transcervically through uterus U, generally under optical direction. The physician directs the distal end of the delivery system toward the ostium O of the fallopian tube F. The uterus U may be irrigated and/or distended. Once the ostium O is located and the delivery system S is oriented toward the ostium, the delivery system S is advanced distally into the ostium.

Figure 7B:
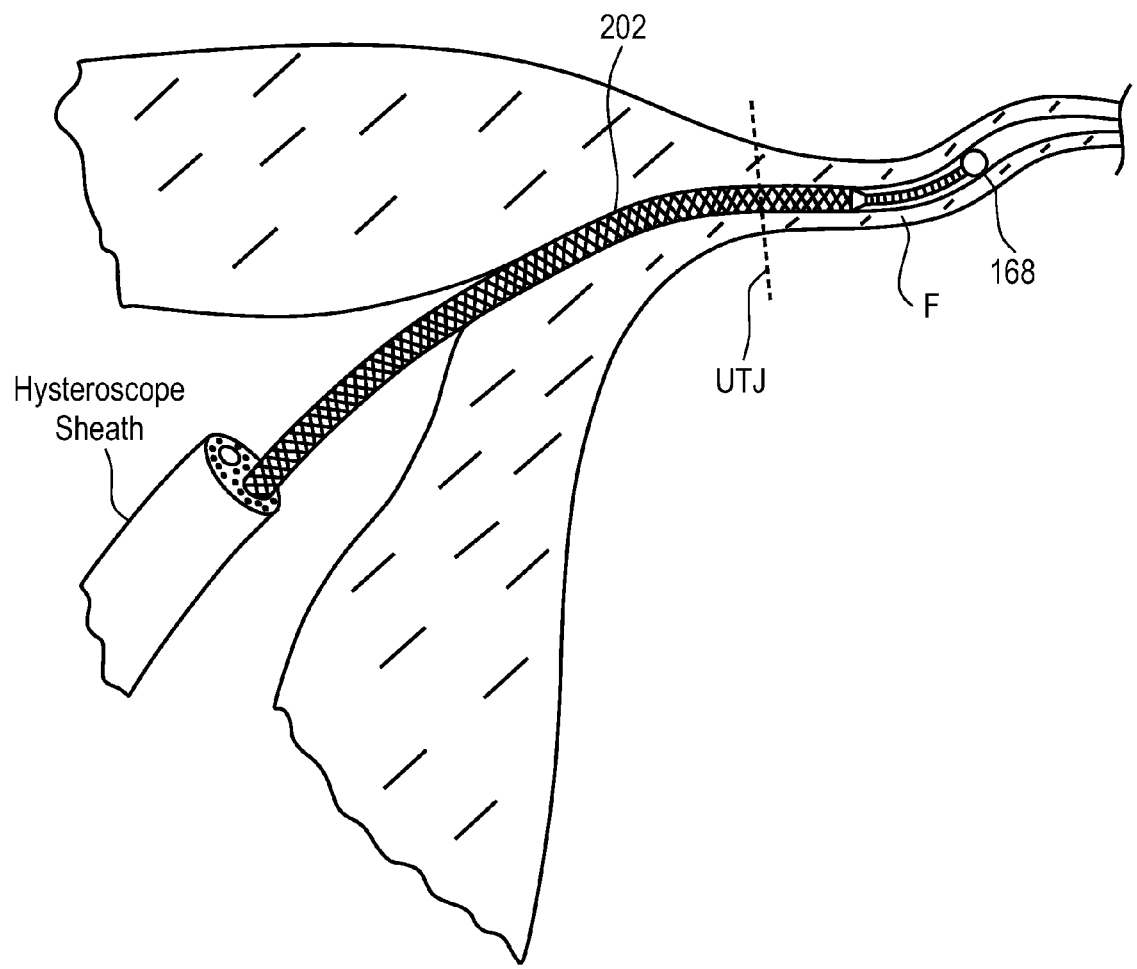

In one embodiment, the distal portion of the contraceptive device acts as a guidewire, while the remainder of the contraceptive device remains covered by the sheath 202, as shown in FIG. 7B. The distal ball tip 168 of the distal portion of the device aids tracking and navigation through the fallopian tube F, while the primary coil structure flexes laterally to track the tortuous bends often found within the fallopian tube. In the exemplary embodiment, a core wire extends into the distal portion to enhance column strength of the distal portion beyond sheath, but does not extend to the ball tip. Hence, the stiffness of distal portion increases proximally, further enhancing the distal portion's ability to track the lumen. In embodiments in which the contraceptive device includes hydrogel at the distal portion of the contraceptive device (e.g., distal ball), the hydrogel will swell during delivery (if it is exposed). The expanded or expanding hydrogel distal ball can improve trackability of the contraceptive device through the bends of the fallopian tube, particularly in those embodiments in which the hydrogel is formulated to improve trackability.

In another embodiment, the contraceptive device will be entirely within the delivery catheter 202 during delivery and positioning.

In the exemplary embodiment, the sheath includes a visual marker which can be seen from the scope of an hysteroscope. The marker is preferably positioned partially within the ostium O and partially within the uterus U, thereby indicating that the contraceptive device is disposed at the target position, as the sheath, core shaft, and contraceptive device are releasably locked together during advancement and positioning. As described above, the marker may comprise a bumper, a structure which extends radially from the sheath to provide a tactile positioning indication.

Figure 7C:
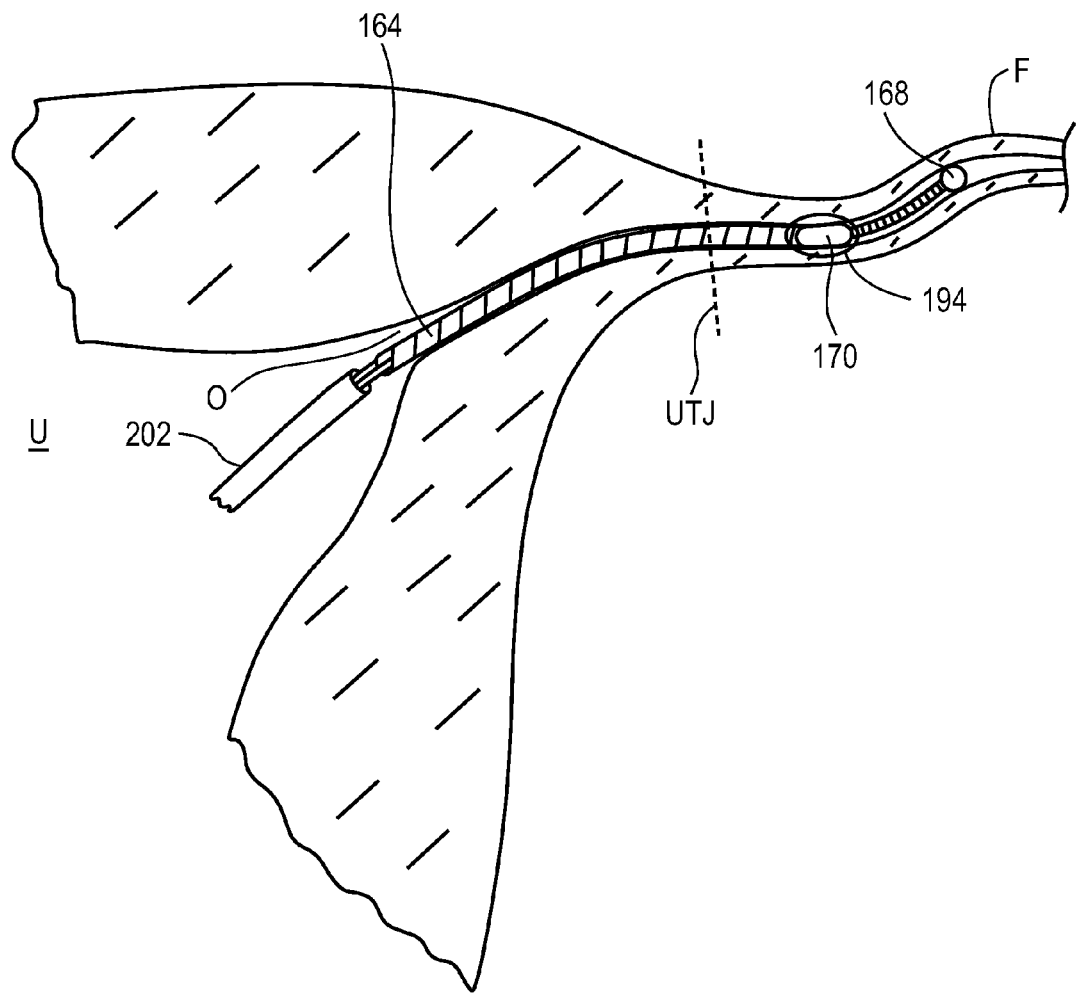
Figure 7D:
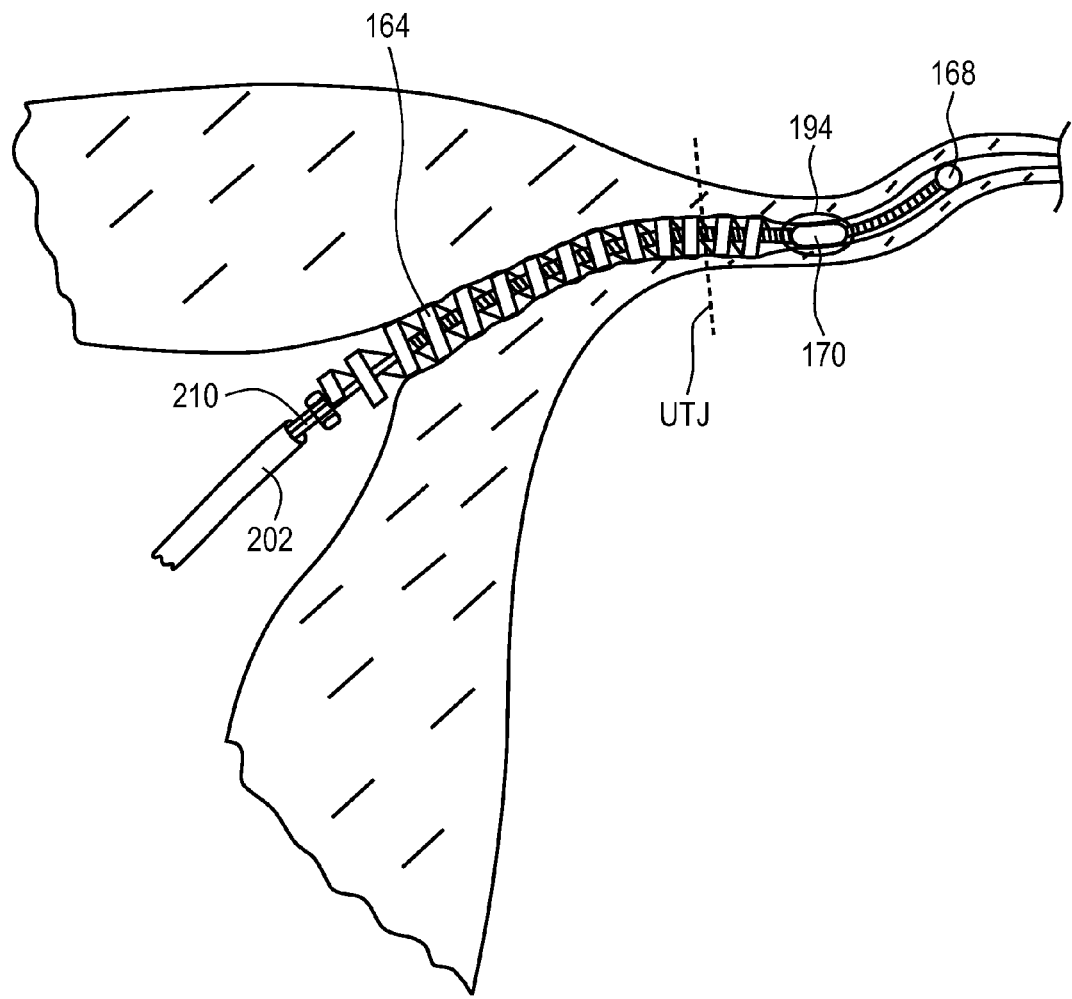
Figure 7E:
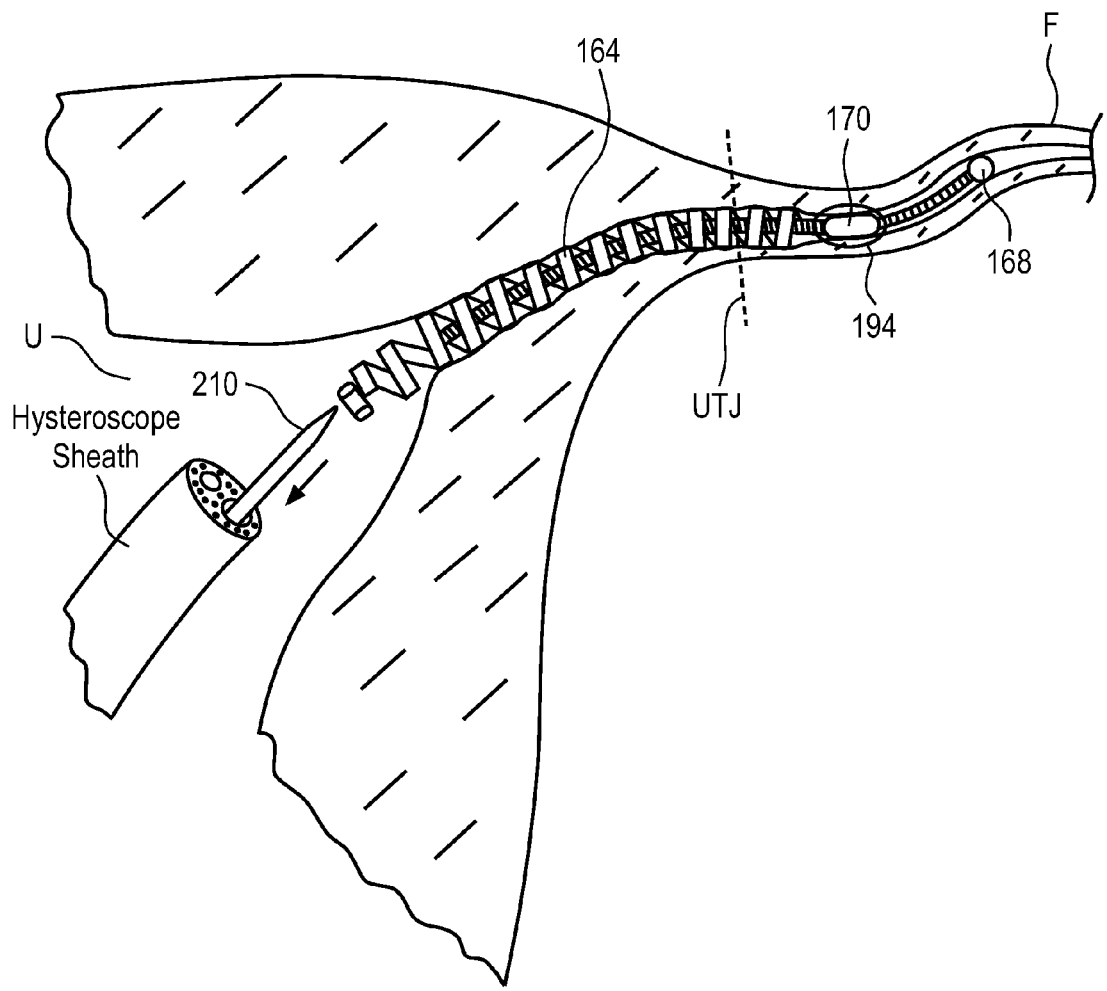

Referring now to FIGS. 7C-7E, the positioned contraceptive device is deployed, in one embodiment, by first withdrawing the sheath of the delivery catheter 202 from over the expandable structure 150, as shown in FIG. 7C. The outer coil 164 of the contraceptive device 150 is separated from the release catheter 210, allowing the outer coil 164 to expand, as shown in FIG. 7D. Once the sheath 202 has been withdrawn from over the expandable structure 150 and the release catheter 210 has been disengaged from the exposed expandable structure, the outer coil 164 resiliently expands and affixes the contraceptive device 150 in place. The hydrogel 194 has, at this point, begun to swell and will at least temporarily block the fallopian tube. The contraceptive device 150 is separated from the remaining components of delivery system, as shown in FIG. 7E.

Figure 7F:
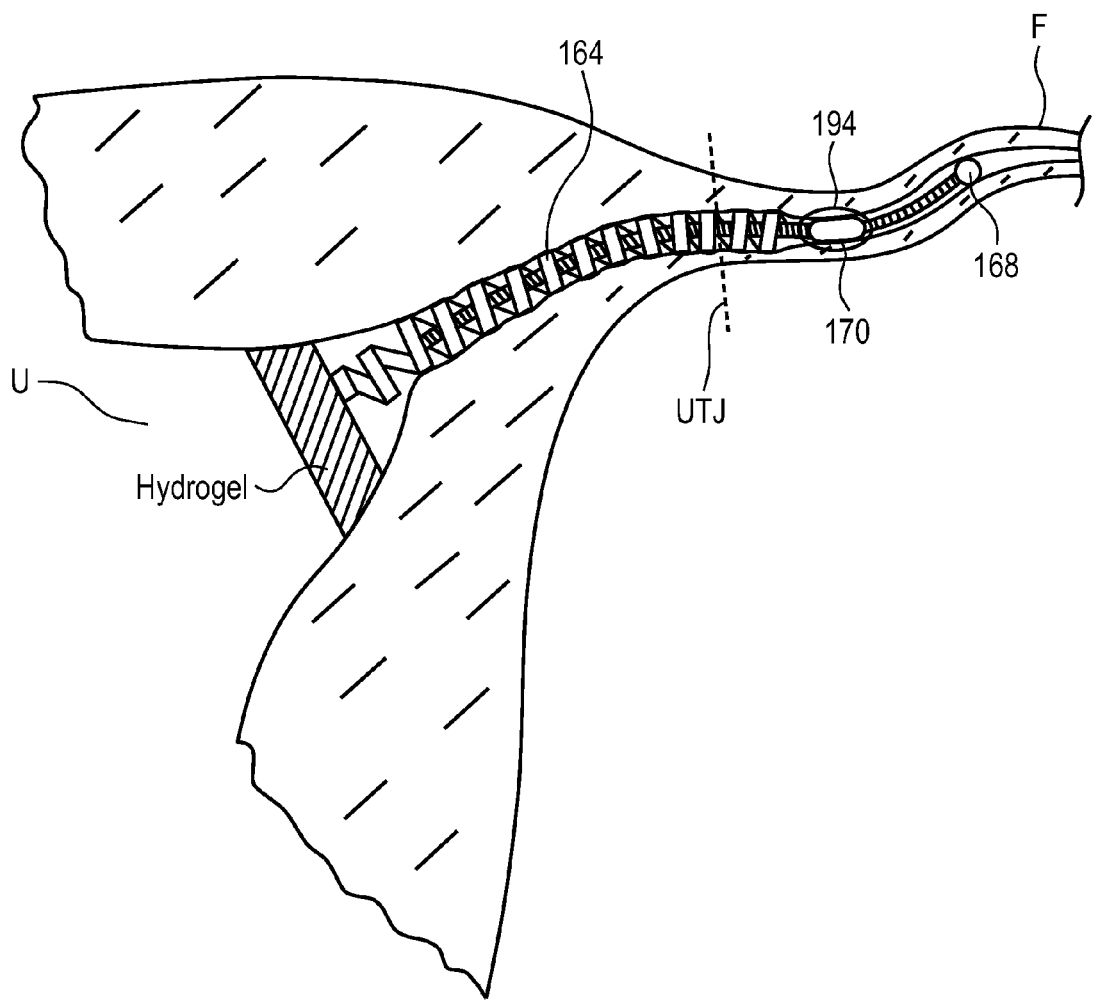
Figure 7G:
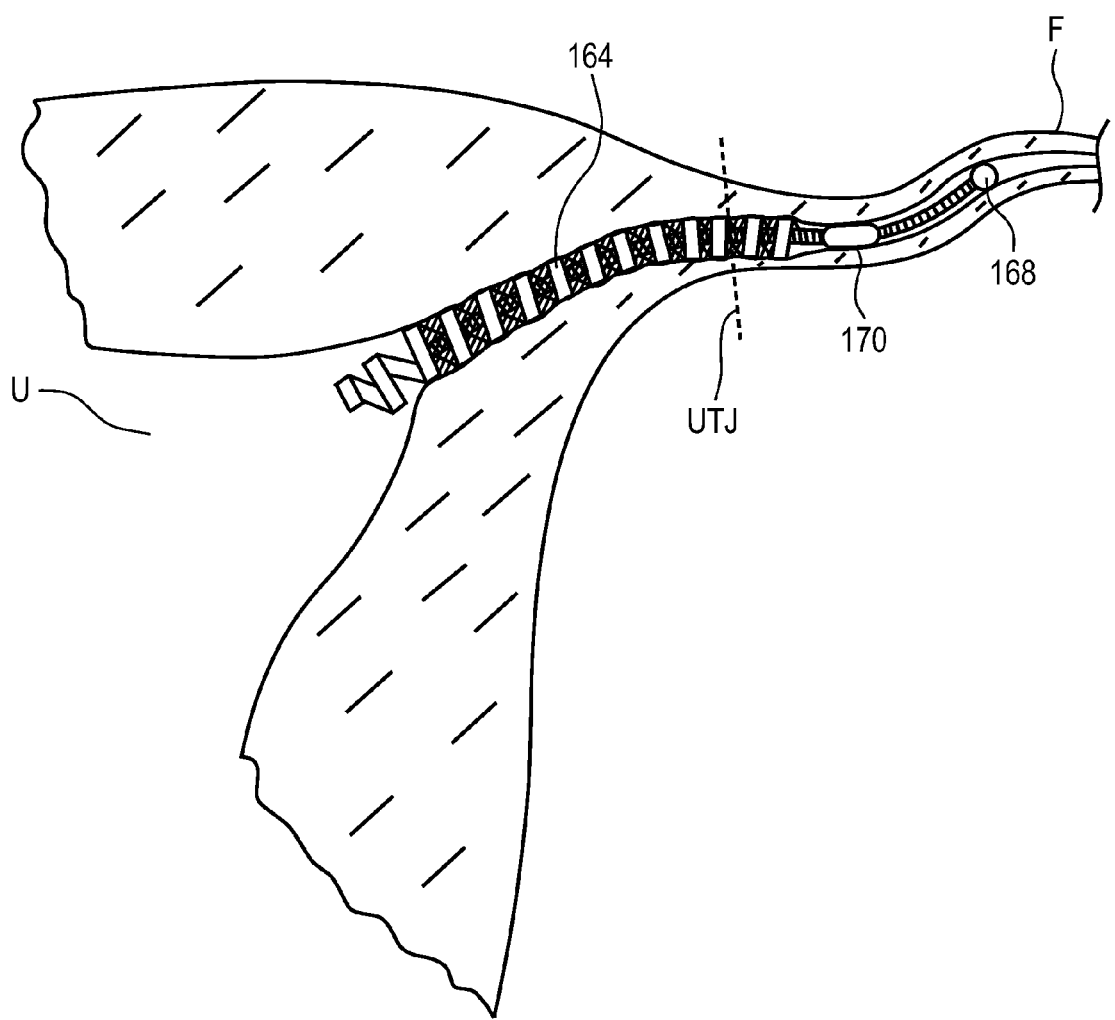

As shown in FIG. 7F, the hydrogel may expand to fill in areas of the fallopian tube and/or ostium to block the ovarian pathway (if hydrogel is present on the proximal end of the device as in the case of the example shown in FIG. 7F). As shown in FIG. 7G, tissue has grown within the implant because of the tissue reaction caused by the tissue ingrowth fibers. As shown in FIG. 7G, the hydrogel is no longer present; in such an embodiment, the hydrogel is biodegradable. It will be appreciated that the hydrogel need not be biodegradable (hydrogel and tissue ingrowth together provide sterilization).

Figure 8A:
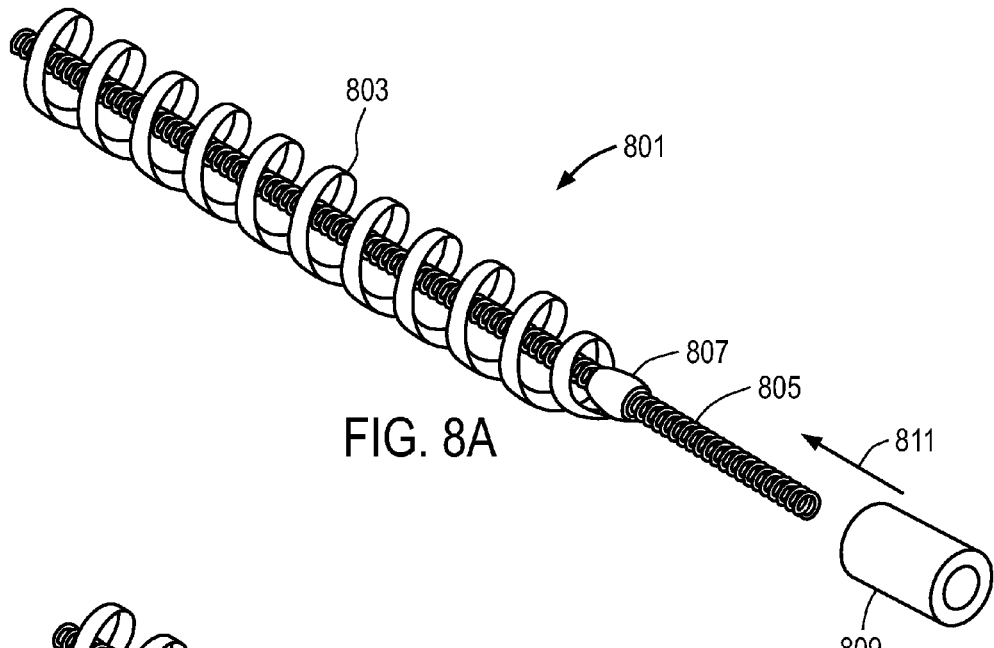
FIG. 8A is a perspective view of a contraceptive device being assembled.
Figure 8B:
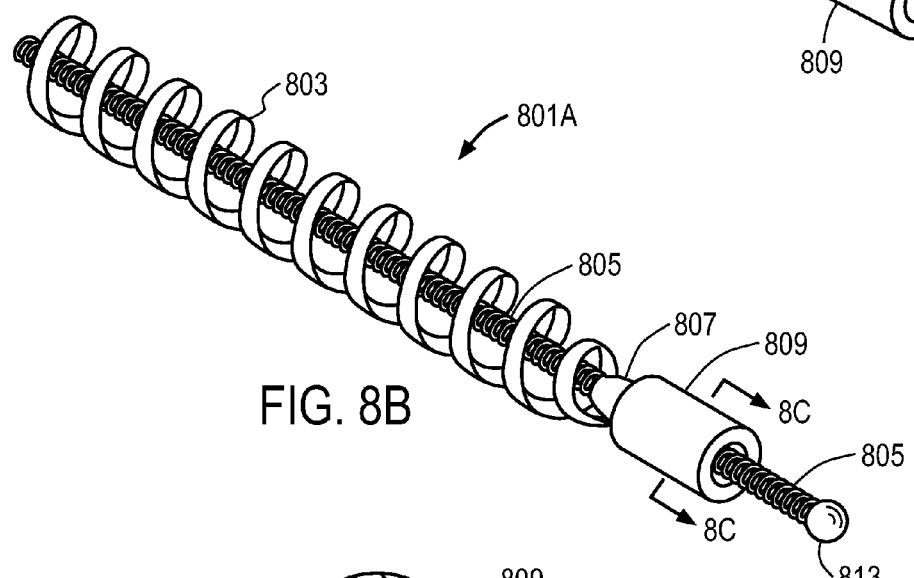
FIG. 8B is a perspective view of the contraceptive device of FIG. 8A after a hydrogel cylinder has been added to the device.
Figure 8C:
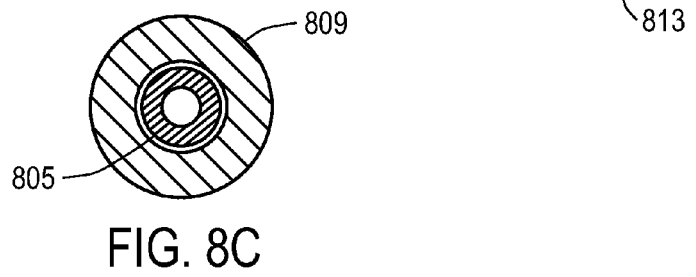
FIG. 8C is a cross-sectional view of the device of FIG. 8B, wherein the cross-section is taken at line 8C-8C in FIG. 8B.

FIGS. 8A, 8B and 8C show another example of an embodiment of a contraceptive device according to one aspect of the invention. The contraceptive device 801 shown in FIG. 8A can be formed from one or more metals or organic polymers and can include Dacron or polyester fibers to act as a tissue ingrowth promoting agent to cause tissue to grow into the device after it has been implanted into a fallopian tube. The Dacron or polyester fibers (or other tissue ingrowth promoting agents) can be attached to one or more components (e.g. the outer coil 803) of the device. The outer coil 803 can be configured to be resilient and self-expanding from a deployed configuration; the outer coil 803 can be restrained within a delivery catheter or sheath and once deployed can radially expand to resiliently engage the walls of a fallopian tube. A delivery shaft or wire in the delivery catheter (not shown) can be removably attached to a proximal end of the inner coil 805; a connection between the proximal end of the inner coil 805 and a delivery shaft or wire can be any one of known or conventional connections that allow the delivery shaft or wire to be removably coupled to the contraceptive device 801. The inner coil 805 and the outer coil 803 can be connected together by a connection mechanism 807 which can be a solder joint. In one implementation of a manufacturing process, a preformed or cast hollow cylinder of hydrogel, such as the hydrogel cylinder 809, can be applied onto the distal end of the inner coil 805 prior to applying the distal ball 813. The application of the cylinder 809 onto the distal end of the inner coil 805 in this manner is represented by arrow 811 which shows how the cylinder 809 can be slid onto the distal end of the inner coil 805. The hydrogel 809 can be slid onto the coil 805 when the hydrogel 809 is in a dehydrated state so that it is not swollen. The hydrogel 809 can be either a non-biodegradable hydrogel or a biodegradable hydrogel. The hydrogel 809 is designed to swell to an enlarged configuration, as described herein, when placed within a fallopian tube. A glue can be applied between the cylinder 809 and the inner coil 805 either before or after sliding the cylinder 809 onto the distal end of the inner coil 805. The inner coil 805 can be stretched before applying the cylinder 809. The glue can be applied to either or both of the cylinder 809 and the inner coil 805.

In one embodiment, the glue can be cyanoacrylate such as Loctite 4541 or 431 or 3211 or a mixture of cyanoacrylate glues from Henkel Corporation. The glue can be cured with or without UV (ultraviolet) light. The glue can be selected to enhance the structural integrity or strength of the hydrogel after the glue has been cured. In one embodiment, the glue, before curing, can be one color and after curing change to another color, and this can assist in determining when the curing process is completed. The hydrogel 809 can be applied onto the coil 805 without glue in some embodiments.

After applying the cylinder 809 onto the coil 805, distal ball 813 can be attached to the coil 805 (for example, by soldering or by gluing the ball 813 onto the distal end of the coil 805). In an alternative embodiment, the ball 813 can be attached to the coil 805 before the hydrogel 809 is applied onto the coil (e.g. if the inner diameter of the hydrogel 809 is larger than the outer diameter of the distal ball 813).

FIG. 8C shows a cross-sectional view of the contraceptive device 801A (shown in FIG. 8B) taken along the line 8C-8C also shown in FIG. 8B. This cross-sectional view shows that the hydrogel 809 concentrically surrounds the inner coil 805. The hydrogel 809 can be formed or cast to fit snugly or loosely around the inner coil 805, and a layer of glue may exist at the interface or gap between the inner coil 805 and the inner diameter of the hydrogel 809.

Figure 8D:
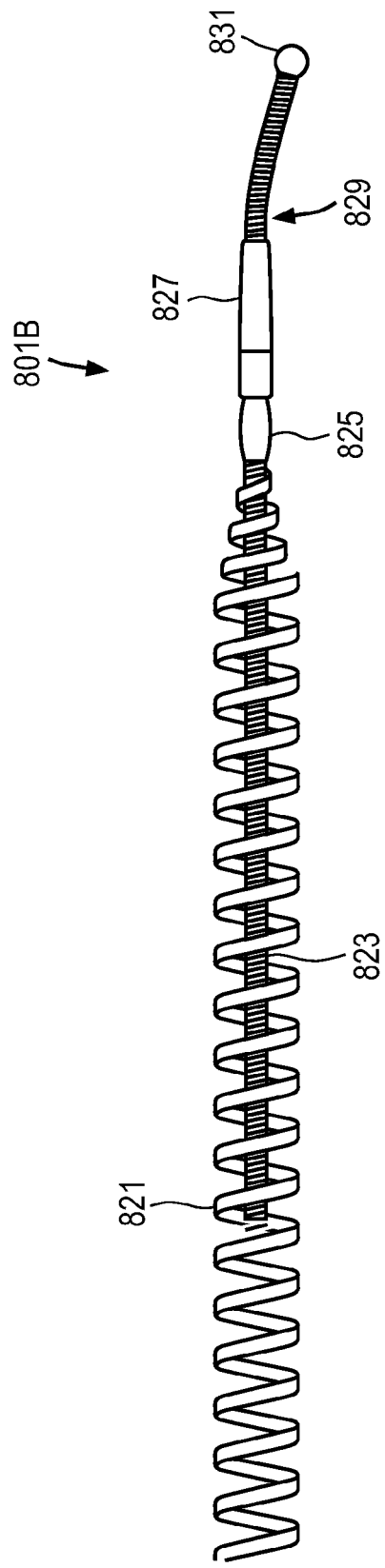
FIG. 8D is a side view of a contraceptive device which is similar to the contraceptive device in FIG. 8B.

FIG. 8D shows, in a side view, an embodiment of a contraceptive device in which the distal end has a preformed bend 829. The preformed bend 829 is designed to assist in the introduction of the device into the ostium of a fallopian tube. The angle of the bend can be from 5° to 20° relative to the remainder of the device 801B. The contraceptive device 801E can include an inner coil 823 and an outer coil 821 which can be similar to inner coil 805 and outer coil 803 of the contraceptive device 801. A connection 825 connects the inner coil 823 to the outer coil 821, and this connection 825 can be similar to the connection mechanism 807. The device 801B also includes hydrogel 827 attached between the distal ball 831 and the connection mechanism 807. The distal ball 831 and the distal ball 813 can both be atraumatic balls designed to act as a distal guide for self-insertion and introduction of the devices into a fallopian tube.

The foregoing description with attached drawings is only illustrative of possible embodiments of the described method and should only be construed as such. Other persons of ordinary skill in the art will realize that many other specific embodiments are possible that fall within the scope and spirit of the present idea. The scope of the invention is indicated by the following claims rather than by the foregoing description. Any and all modifications which come within the meaning and range of equivalency of the following claims are to be considered within their scope.

The invention claimed is:

1. A system for occluding a tubular body lumen comprising:

a deployment sheath;

an occlusion device at least partially disposed within the deployment sheath, the occlusion device comprising:
  an expandable implant having a proximal end and a distal end, wherein a portion of the expandable implant comprises hydrogel; and
  tissue in-growth promoting agent on the expandable implant, wherein the expandable implant comprises an outer coil, an inner coil, a flexible tip, a distal solder joint connecting the outer coil, inner coil and flexible tip at the distal end and a detachable release joint at the proximal end; and
a hydrophobic material at a distal end of the deployment sheath, wherein the distal end of the occlusion device extends beyond the distal end of the deployment sheath while the hydrophobic material protects the hydrogel from swelling upon exposure of the distal end of the deployment sheath to a physiological environment, and the hydrophobic material is pierceable by the occlusion device to deliver the occlusion device through the distal end of the deployment sheath.

2. The system of claim 1, wherein the hydrogel is formulated to improve trackability within a female reproductive anatomy.

3. The system of claim 2, wherein the expandable implant further comprises a proximal solder joint connected to the inner coil and detachable release.

4. The system of claim 3, wherein the hydrogel coats the proximal solder joint.

5. The system of claim 2, wherein the hydrogel coats the detachable release joint.

6. The system of claim 2, wherein the hydrogel coats the distal solder joint.

7. The system of claim 2, wherein the flexible tip comprises a distal ball.

8. The system of claim 2, wherein the flexible tip comprises a preformed bend.

9. The system of claim 1 wherein the hydrogel is a preformed hollow cylinder that concentrically surrounds the inner coil.

10. The system of claim 9, wherein the preformed hollow cylinder is attached to the inner coil with a glue.

11. The system of claim 1, wherein the tissue in-growth promoting agent comprise polyester fibers.

12. The system of claim 1, wherein the hydrogel is biodegradable.

13. A system for occluding a tubular body lumen comprising:
  a deployment sheath;
  an occlusion device at least partially disposed within the deployment sheath, the occlusion device comprising:
    an inner coil;
    an expandable outer coil;
    a flexible tip;
    a distal joint connecting the outer coil, inner coil and flexible tip;
    a detachable release joint;
    tissue in-growth promoting fibers between the inner coil and the expandable outer coil; and
    wherein one or more of the flexible tip, distal joint or detachable release joint comprises hydrogel; and
  a hydrophobic material at a distal end of the deployment sheath, wherein the distal end of the occlusion device extends beyond the distal end of the deployment sheath while the hydrophobic material protects the hydrogel from swelling upon exposure of the distal end of the deployment sheath to a physiological environment, and the hydrophobic material is pierceable by the occlusion device to deliver the occlusion device through the distal end of the deployment sheath.

14. The system of claim 13, further comprising a proximal solder joint between the detachable release joint and the inner coil and wherein the distal joint is a solder joint.

15. The system of claim 14, wherein the proximal solder joint comprises the hydrogel.

16. The system of claim 13 wherein the hydrogel is a preformed hollow cylinder that concentrically surrounds the inner coil.

17. The system of claim 16, wherein the preformed hollow cylinder is attached to the inner coil with a glue.

18. The contraceptive delivery system of claim 13, wherein one or more of the flexible tip, distal joint or detachable release joint is coated with the hydrogel.

19. The system of claim 13, wherein the flexible tip comprises a distal ball.

20. The system of claim 13, wherein the flexible tip comprises a preformed bend distal ball, and wherein the distal ball is hydrogel.

21. The system of claim 13, wherein the tissue in-growth fibers comprise a polyester fiber.

22. The system of claim 13, wherein the hydrogel is biodegradable.

23. A system for delivering an implant to a tubular body lumen comprising:
  a delivery catheter having a distal end and a proximal end;
  an expandable implant releasably coupled with the delivery catheter, the expandable implant comprising hydrogel and tissue ingrowth fibers; and
  a hydrophobic material at a distal end of the delivery catheter, wherein a distal end of the expandable implant extends beyond the distal end of the delivery catheter while the hydrophobic material protects the hydrogel from swelling upon exposure of the distal end of the delivery catheter to a physiological environment, and the hydrophobic material is pierceable by the expandable implant to deliver the expandable implant through the distal end of the delivery catheter.

24. The system of claim 23 wherein the expandable implant comprises an inner coil and an expandable outer coil, and the hydrogel is a preformed hollow cylinder that concentrically surrounds the inner coil.

25. The system of claim 24, wherein the preformed hollow cylinder is attached to the inner coil with a glue.

26. The system of claim 23, wherein the hydrophobic material is a coating at the distal end of the delivery catheter.

27. The system of claim 23, wherein the hydrophobic material is a membrane covering the distal end of the delivery catheter.

28. A method of delivering an expandable implant to a tubular body lumen comprising:
  delivering a catheter to an ovarian pathway, the catheter having an expandable implant releasably coupled with the catheter, the expandable implant comprising hydrogel and tissue ingrowth promoting fibers, wherein a hydrophobic material is at a distal end of the catheter, and a distal end of the expandable implant extends beyond the distal end of the catheter while the hydrophobic material protects the hydrogel from swelling upon exposure of the distal end of the catheter to a physiological environment in the ovarian pathway;
  piercing the hydrophobic material with the expandable implant;
  pushing the expandable implant through the hydrophobic material and through the distal end of the catheter; and
  expanding the expandable implant in the ovarian pathway.

29. The system of claim 28 wherein the expandable implant comprises an inner coil and an expandable outer coil, and the hydrogel is a preformed hollow cylinder that concentrically surrounds the inner coil.

30. The system of claim 29, wherein the preformed hollow cylinder is attached to the inner coil with a glue.

31. The method of claim 28, wherein further comprising allowing the hydrogel to expand to block the ovarian pathway after pushing the expandable implant through the catheter.

32. The method of claim 28, wherein further comprising allowing the tissue ingrowth promoting fibers to incite a reaction in the ovarian pathway to block the ovarian pathway.

33. The method of claim 28, further comprising allowing the hydrogel coating to biodegrade.

34. The method of claim 28, wherein the hydrophobic material encapsulates a length of the expandable implant.

35. The method of claim 28, wherein the hydrophobic material is a coating at the distal end of the catheter and wherein the hydrophobic material rapidly dissolves in the physiologic environment.

36. The method of claim 28, wherein the hydrophobic material is a membrane covering the distal end of the catheter.

37. A system for occluding a tubular body lumen comprising:
a deployment sheath;
an occlusion device at least partially disposed within the deployment sheath, the occlusion device comprising:
a primary coil structure having an outer coil and an inner coil coaxial with the outer coil, the primary coil structure being laterally flexible, the outer coil bring self expandable from a constrained configuration;
a non-traumatic tip attached to the primary coil structure at a distal joint;
tissue in-growth promoting fibers disposed between the outer coil and the inner coil; and
hydrogel disposed adjacent to the distal joint; and
a hydrophobic material at a distal end of the deployment sheath, wherein a distal end of the occlusion device extends beyond the distal end of the deployment sheath while the hydrophobic material protects the hydrogel from swelling upon exposure of the distal end of the deployment sheath to a physiological environment, and the hydrophobic material is pierceable by the occlusion device to deliver the occlusion device through the distal end of the deployment sheath.

38. The system of claim 37 further comprising a core wire extending to the distal joint.

39. The system of claim 38 wherein the stiffness of the distal portion of the core wire increases proximally.

40. The system of claim 37 wherein the hydrogel is disposed proximally to the distal joint.

41. The system of claim 40 wherein the superelastic material comprises a NiTi alloy.

42. The system of claim 37 wherein the hydrogel is a preformed hollow cylinder that concentrically surrounds the inner coil.

43. The system of claim 42, wherein the preformed hollow cylinder is attached to the inner coil with a glue.

44. The system of claim 37 wherein the hydrogel is formulated to improve trackability of the contraceptive device during delivery of the occlusion device into a fallopian tube.

45. The system of claim 37 wherein the non-traumatic tip is ball-shaped.

46. The system of claim 37 wherein the outer coil comprises a superelastic material.

47. The system of claim 37 wherein the non-traumatic tip includes a slight preformed bend.

48. The system of claim 37 wherein the hydrophobic material encapsulates a length of the occlusion device.

49. The system of claim 37 wherein the deployment sheath is disposed only proximally from the distal joint.

* * * * *